(12) United States Patent
Torigoe et al.

(10) Patent No.: US 7,141,393 B2
(45) Date of Patent: ***Nov. 28, 2006

(54) INTERLEUKIN-18-RECEPTOR PROTEINS

(75) Inventors: Kakuji Torigoe, Okayama (JP); Shimpei Ushio, Okayama (JP); Toshio Kunikata, Okayama (JP); Masashi Kurimoto, Okayama (JP)

(73) Assignee: Kabushiki Kaisha Hayashibara Seibutsu Kagaku Kenkyujo, Okayama (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/996,140

(22) Filed: Dec. 22, 1997

(65) Prior Publication Data

US 2003/0190318 A1    Oct. 9, 2003

(30) Foreign Application Priority Data

| Dec. 26, 1996 | (JP) | 8-356426 |
| Feb. 21, 1997 | (JP) | 9-052526 |
| Jun. 6, 1997 | (JP) | 9-163490 |
| Jul. 28, 1997 | (JP) | 9-215490 |

(51) Int. Cl.
*C12P 21/04* (2006.01)

(52) U.S. Cl. ............... 435/70.1; 530/70.21; 530/412; 530/350; 514/2

(58) Field of Classification Search ............... 530/350; 514/2
See application file for complete search history.

(56) References Cited

U.S. PATENT DOCUMENTS 5,776,731 A * 7/1998 Parnet et al. ............... 435/69.1

FOREIGN PATENT DOCUMENTS

| EP | 0692536 A2 | 1/1996 |
| EP | 0712931 A2 | 5/1996 |
| JP | 827189 | 1/1996 |
| JP | 8193098 | 7/1996 |
| WO | 9731010 | 8/1997 |

OTHER PUBLICATIONS

Torigoe, K., et al. (1997) *J. Biol. Chem.* 272(41): 25737-42, Oct. 1997.*
P. Parnet et al., "IL-Rrp is a novel receptor-like molecule similar to the type I interleukin-1 receptor and its homologues T1/ST2 and IL-1R AcP", The Journal of Biological Chemistry, vol. 271, No. 8, pp. 3967-3970, Feb. 23, 1996.
H. Okamura et al., "Cloning of a new cytokine that induces IFN-∩ production by T cells", Nature, vol. 378, No. 6552, pp. 88-91, Nov. 2, 1995.
S. Ushio et al., "Cloning of the cDNA for Human IFN-∩-inducing factor, expression in *Escherichia coli*, and studies on the biologic activities of the protein", The Journal of Immunology, vol. 156, pp. 4274-4279, 1996.
S. Toyama et al., "Tan-Clone-Kotai-Jikken-Manual", Kodansha Scientific, Ltd., pp. 105-152, 1991.
P. Tijssen, "Laboratory Techniques in biochemistry and molecular biology: Practice and theory of enzyme immunoassays", Tokyo-Kagaku-Dojin, pp. 196-348, 1989.
F. Lan et al., "Extended fitness of variable region primers by a novel PCR protocol", Journal of Immunological Methods, vol. 195, pp. 27-32, 1996.
S. Jones et al., "Material and methods/ Rapid PCR-cloning of full-length mouse immunoglobulin variable regions", Bio/Technology, vol. 9, pp. 88-89, Jan. 1991.
S. Paul, "Antibody engineering protocols", Methods in Molecular Biology, vol. 51, 1995.
J. Minowada, "Leukemia cell lines", Cancer Review, vol. 10, pp. 1-18, 1988.

* cited by examiner

*Primary Examiner*—Gary B. Nickol
*Assistant Examiner*—Dong Jiang
(74) *Attorney, Agent, or Firm*—Browdy & Neimark, PLLC

(57) ABSTRACT

Disclosed are a receptor protein which recognize a novel cytokine, i.e., interleukin-18, a monoclonal antibody specific to the protein, and uses thereof. The receptor protein is useful as pharmaceutical to treat and prevent autoimmune and allergic disease because it suppresses and regulates excessive immunoreaction. The monoclonal antibody specifically reacts with interleukin-18, exhibiting efficacy in purification, detection and inhibition of interleukin-18.

7 Claims, 5 Drawing Sheets

Lane 1 : Molecular weight markers
Lane 2 : Sample (with monoclonal antibody)
Lane 3 : Sample (without monoclonal antibody)
Lane 4 : Molecular weight markers

SEQUENCE LISTING (1) GENERAL INFORMATION:

(iii) NUMBER OF SEQUENCES: 31

(2) INFORMATION FOR SEQ ID NO:1:

(i) SEQUENCE CHARACTERISTICS:
      (A) LENGTH:157
      (B) TYPE:amino acid
      (D) TOPOLOGY:linear (ii) MOLECULE TYPE:peptide (xi) SEQUENCE DESCRIPTION:SEQ ID NO:1:

```
Tyr Phe Gly Lys Leu Glu Ser Lys Leu Ser Val Ile Arg Asn Leu Asn
 1               5                  10                  15
Asp Gln Val Leu Phe Ile Asp Gln Gly Asn Arg Pro Leu Phe Glu Asp
                20                  25                  30
Met Thr Asp Ser Asp Cys Arg Asp Asn Ala Pro Arg Thr Ile Phe Ile
            35                  40                  45
Ile Ser Met Tyr Lys Asp Ser Gln Pro Arg Gly Met Ala Val Thr Ile
        50                  55                  60
Ser Val Lys Cys Glu Lys Ile Ser Xaa Leu Ser Cys Glu Asn Lys Ile
65                  70                  75                  80
Ile Ser Phe Lys Glu Met Asn Pro Pro Asp Asn Ile Lys Asp Thr Lys
                85                  90                  95
Ser Asp Ile Ile Phe Phe Gln Arg Ser Val Pro Gly His Asp Asn Lys
            100                 105                 110
Met Gln Phe Glu Ser Ser Ser Tyr Glu Gly Tyr Phe Leu Ala Cys Glu
        115                 120                 125
Lys Glu Arg Asp Leu Phe Lys Leu Ile Leu Lys Lys Glu Asp Glu Leu
    130                 135                 140
Gly Asp Arg Ser Ile Met Phe Thr Val Gln Asn Glu Asp
145                 150                 155
```

(2) INFORMATION FOR SEQ ID NO:2:

(i) SEQUENCE CHARACTERISTICS:
        (A) LENGTH:157
        (B) TYPE:amino acid
        (D) TOPOLOGY:linear (ii) MOLECULE TYPE:peptide (xi) SEQUENCE DESCRIPTION:SEQ ID NO:2:

```
Asn Phe Gly Arg Leu His Cys Thr Thr Ala Val Ile Arg Asn Ile Asn
 1               5                  10                  15
Asp Gln Val Leu Phe Val Asp Lys Arg Gln Pro Val Phe Glu Asp Met
            20                  25                  30
Thr Asp Ile Asp Gln Ser Ala Ser Glu Pro Gln Thr Arg Leu Ile Ile
        35                  40                  45
Tyr Met Tyr Lys Asp Ser Glu Val Arg Gly Leu Ala Val Thr Leu Ser
 50                  55                  60
Val Lys Asp Ser Lys Xaa Ser Thr Leu Ser Cys Lys Asn Lys Ile Ile
65                  70                  75                  80
Ser Phe Glu Glu Met Asp Pro Pro Glu Asn Ile Asp Asp Ile Gln Ser
                85                  90                  95
Asp Leu Ile Phe Phe Gln Lys Arg Val Pro Gly His Asn Lys Met Glu
            100                 105                 110
Phe Glu Ser Ser Leu Tyr Glu Gly His Phe Leu Ala Cys Gln Lys Glu
        115                 120                 125
Asp Asp Ala Phe Lys Leu Ile Leu Lys Lys Lys Asp Glu Asn Gly Asp
130                 135                 140
Lys Ser Val Met Phe Thr Leu Thr Asn Leu His Gln Ser
145                 150                 155
```

(2) INFORMATION FOR SEQ ID NO:3:

(i) SEQUENCE CHARACTERISTICS:
        (A) LENGTH:5 amino acids
        (B) TYPE:amino acid
        (D) TOPOLOGY:linear (ii) MOLECULE TYPE:peptide (v) FRAGMENT TYPE:internal fragment (xi) SEQUENCE DESCRIPTION:SEQ ID NO:3:

```
Trp His Ala Ser Lys
 1               5
```

(2) INFORMATION FOR SEQ ID NO:4:

(i) SEQUENCE CHARACTERISTICS:
        (A) LENGTH:7 amino acids
        (B) TYPE:amino acid
        (D) TOPOLOGY:linear (ii) MOLECULE TYPE:peptide (v) FRAGMENT TYPE:internal fragment (xi) SEQUENCE DESCRIPTION:SEQ ID NO:4:

```
Ile Met Thr Pro Glu Gly Lys
 1               5
```

(2) INFORMATION FOR SEQ ID NO:5:

(i) SEQUENCE CHARACTERISTICS:
        (A) LENGTH:13 amino acids
        (B) TYPE:amino acid
        (D) TOPOLOGY:linear (ii) MOLECULE TYPE:peptide (v) FRAGMENT TYPE:internal fragment (xi) SEQUENCE DESCRIPTION:SEQ ID NO:5:

```
Ser Ser Gly Ser Gln Glu His Val Glu Leu Asn Pro Arg
 1               5                  10
```

(2) INFORMATION FOR SEQ ID NO:6:

(i) SEQUENCE CHARACTERISTICS:

```
        (A) LENGTH:4 amino acids
        (B) TYPE:amino acid
        (D) TOPOLOGY:linear (ii) MOLECULE TYPE:peptide (v) FRAGMENT TYPE:internal fragment (xi) SEQUENCE DESCRIPTION:SEQ ID NO:6:
Ser Trp Tyr Lys
 1

(2) INFORMATION FOR SEQ ID NO:7:

(i) SEQUENCE CHARACTERISTICS:
        (A) LENGTH:10 amino acids
        (B) TYPE:amino acid
        (D) TOPOLOGY:linear (ii) MOLECULE TYPE:peptide (v) FRAGMENT TYPE:internal fragment (xi) SEQUENCE DESCRIPTION:SEQ ID NO:7:
Leu Asn His Val Ala Val Glu Leu Gly Lys
 1               5                  10

(2) INFORMATION FOR SEQ ID NO:8:

(i) SEQUENCE CHARACTERISTICS:
        (A) LENGTH:6 amino acids
        (B) TYPE:amino acid
        (D) TOPOLOGY:linear (ii) MOLECULE TYPE:peptide (v) FRAGMENT TYPE:internal fragment (xi) SEQUENCE DESCRIPTION:SEQ ID NO:8:
Ser Phe Ile Leu Val Arg
 1               5

(2) INFORMATION FOR SEQ ID NO:9:

(i) SEQUENCE CHARACTERISTICS:
        (A) LENGTH:15 amino acids
        (B) TYPE:amino acid
        (D) TOPOLOGY:linear (ii) MOLECULE TYPE:peptide (v) FRAGMENT TYPE:internal fragment (xi) SEQUENCE DESCRIPTION:SEQ ID NO:9:
Thr Val Lys Pro Gly Arg Asp Glu Pro Glu Val Leu Pro Val Leu
 1               5                  10                  15

(2) INFORMATION FOR SEQ ID NO:10:

(i) SEQUENCE CHARACTERISTICS:
        (A) LENGTH:11 amino acids
        (B) TYPE:amino acid
        (D) TOPOLOGY:linear (ii) MOLECULE TYPE:peptide (v) FRAGMENT TYPE:internal fragment (xi) SEQUENCE DESCRIPTION:SEQ ID NO:10:
Ser Asn Ile Val Pro Val Leu Leu Gly Pro Lys
 1               5                  10

(2) INFORMATION FOR SEQ ID NO:11:

(i) SEQUENCE CHARACTERISTICS:
        (A) LENGTH:119 amino acids
        (B) TYPE:amino acid
        (D) TOPOLOGY:linear
```

(ii) MOLECULE TYPE:peptide (xi) SEQUENCE DESCRIPTION:SEQ ID NO:11:
Glu Val Gln Leu Gln Gln Ser Gly Ala Glu Leu Val Lys Pro Gly Ala
 1               5                  10                  15
Ser Val Lys Leu Ser Cys Thr Thr Ser Gly Phe Asn Ile Lys Asp Ile
                20                  25                  30
Tyr Ile Tyr Trp Val Lys Gln Arg Pro Glu Gln Gly Leu Glu Trp Val
            35                  40                  45
Gly Arg Ile Asp Pro Ala Asn Gly Asp Thr Lys Tyr Gly Pro Asn Phe
        50                  55                  60
Gln Asp Lys Ala Thr Ile Thr Ala Asp Thr Ser Ser Asn Thr Ala Tyr
 65                 70                  75                  80
Leu Gln Leu Arg Ser Leu Thr Ser Glu Asp Thr Ala Val Tyr Tyr Cys
                85                  90                  95
Ala Arg Arg Gly Asn Tyr Gly Ala Gly Phe Gly Tyr Trp Gly Gln Gly
                100                 105                 110
Thr Leu Val Thr Val Ser Ala
        115

(2) INFORMATION FOR SEQ ID NO:12:

(i) SEQUENCE CHARACTERISTICS:
        (A) LENGTH:108 amino acids
        (B) TYPE:amino acid
        (D) TOPOLOGY:linear (ii) MOLECULE TYPE:peptide (xi) SEQUENCE DESCRIPTION:SEQ ID NO:12:
Asp Ile Gln Met Thr Gln Ser Pro Ala Ser Leu Ser Ala Ser Val Gly
 1               5                  10                  15
Glu Thr Val Thr Ile Thr Cys Arg Ala Ser Gly Asn Ile His Asn Tyr
                20                  25                  30
Leu Ala Trp Tyr Gln Gln Arg Gln Gly Lys Ser Pro Gln Ile Leu Val
            35                  40                  45
Tyr Asn Ala Lys Thr Leu Ala Asp Gly Val Ser Ser Arg Phe Ser Gly
        50                  55                  60
Ser Gly Ser Gly Thr Gln Tyr Ser Leu Asn Ile Asn Ser Leu Gln Pro
 65                 70                  75                  80
Glu Asp Phe Gly Thr Tyr Phe Cys Gln His Phe Trp Ser Thr Pro Tyr
                85                  90                  95
Thr Phe Gly Gly Gly Thr Lys Leu Glu Ile Lys Arg
                100                 105

(2) INFORMATION FOR SEQ ID NO:13:

(i) SEQUENCE CHARACTERISTICS:
        (A) LENGTH:10 amino acids
        (B) TYPE:amino acid
        (D) TOPOLOGY:linear (ii) MOLECULE TYPE:peptide (v) FRAGMENT TYPE:internal fragment (xi) SEQUENCE DESCRIPTION:SEQ ID NO:13:
Gly Phe Asn Ile Lys Asp Ile Tyr Ile Tyr
 1               5                  10

(2) INFORMATION FOR SEQ ID NO:14:

(i) SEQUENCE CHARACTERISTICS:
        (A) LENGTH:18 amino acids
        (B) TYPE:amino acid
        (D) TOPOLOGY:linear (ii) MOLECULE TYPE:peptide (v) FRAGMENT TYPE:internal fragment (xi) SEQUENCE DESCRIPTION:SEQ ID NO:14:
Arg Ile Asp Pro Ala Asn Gly Asp Thr Lys Tyr Gly Pro Asn Phe Gln
 1               5                  10                  15
Asp Lys (2) INFORMATION FOR SEQ ID NO:15:

(i) SEQUENCE CHARACTERISTICS:

(A) LENGTH:10 amino acids
        (B) TYPE:amino acid
        (D) TOPOLOGY:linear (ii) MOLECULE TYPE:peptide (v) FRAGMENT TYPE:internal fragment (xi) SEQUENCE DESCRIPTION:SEQ ID NO:15:
Arg Gly Asn Tyr Gly Ala Gly Phe Gly Tyr
 1               5                  10

(2) INFORMATION FOR SEQ ID NO:16:

(i) SEQUENCE CHARACTERISTICS:
        (A) LENGTH:11 amino acids
        (B) TYPE:amino acid
        (D) TOPOLOGY:linear (ii) MOLECULE TYPE:peptide (v) FRAGMENT TYPE:internal fragment (xi) SEQUENCE DESCRIPTION:SEQ ID NO:16:
Arg Ala Ser Gly Asn Ile His Asn Tyr Leu Ala
 1               5                  10

(2) INFORMATION FOR SEQ ID NO:17:

(i) SEQUENCE CHARACTERISTICS:
        (A) LENGTH:7 amino acids
        (B) TYPE:amino acid
        (D) TOPOLOGY:linear (ii) MOLECULE TYPE:peptide (v) FRAGMENT TYPE:internal fragment (xi) SEQUENCE DESCRIPTION:SEQ ID NO:17:
Asn Ala Lys Thr Leu Ala Asp
 1               5

(2) INFORMATION FOR SEQ ID NO:18:

(i) SEQUENCE CHARACTERISTICS:
        (A) LENGTH:9 amino acids
        (B) TYPE:amino acid
        (D) TOPOLOGY:linear (ii) MOLECULE TYPE:peptide (v) FRAGMENT TYPE:internal fragment (xi) SEQUENCE DESCRIPTION:SEQ ID NO:18:
Gln His Phe Trp Ser Thr Pro Tyr Thr
 1               5

(2) INFORMATION FOR SEQ ID NO:19:

(i) SEQUENCE CHARACTERISTICS:
        (A) LENGTH:357 base pairs
        (B) TYPE:nucleic acid
        (C) STRANDEDNESS:double
        (D) TOPOLOGY:linear (ii) MOLECULE TYPE:cDNA (ix) FEATURE:
        (A) NAME/KEY:mat peptide
        (B) LOCATION:1..357
        (C) IDENTIFICATION METHOD:E (xi) SEQUENCE DESCRIPTION:SEQ ID NO:19:
GAG GTT CAG CTG CAG CAG TCT GGG GCA GAG CTT GTG AAG CCA GGG GCC      48
Glu Val Gln Leu Gln Gln Ser Gly Ala Glu Leu Val Lys Pro Gly Ala
 1               5                  10                  15
TCA GTC AAA TTG TCC TGC ACA ACT TCT GGC TTC AAC ATC AAA GAC ATA      96
Ser Val Lys Leu Ser Cys Thr Thr Ser Gly Phe Asn Ile Lys Asp Ile
            20                  25                  30

```
TAT ATC TAC TGG GTG AAA CAG AGG CCT GAA CAG GGC CTG GAG TGG GTT      144
Tyr Ile Tyr Trp Val Lys Gln Arg Pro Glu Gln Gly Leu Glu Trp Val
        35                  40                  45
GGA AGG ATT GAT CCT GCG AAT GGT GAT ACT AAA TAT GGC CCG AAT TTC      192
Gly Arg Ile Asp Pro Ala Asn Gly Asp Thr Lys Tyr Gly Pro Asn Phe
 50                  55                  60
CAG GAC AAG GCC ACT ATA ACA GCA GAC ACA TCC TCC AAC ACA GCC TAC      240
Gln Asp Lys Ala Thr Ile Thr Ala Asp Thr Ser Ser Asn Thr Ala Tyr
 65                  70                  75                  80
CTG CAG CTT CGT AGC CTG ACA TCT GAG GAC ACT GCC GTC TAT TAC TGT      288
Leu Gln Leu Arg Ser Leu Thr Ser Glu Asp Thr Ala Val Tyr Tyr Cys
                 85                  90                  95
GCT AGA CGG GGT AAC TAC GGG GCG GGG TTT GGT TAC TGG GGC CAA GGG      336
Ala Arg Arg Gly Asn Tyr Gly Ala Gly Phe Gly Tyr Trp Gly Gln Gly
                100                 105                 110
ACT CTG GTC ACT GTC TCT GCA                                          357
Thr Leu Val Thr Val Ser Ala
            115

(2) INFORMATION FOR SEQ ID NO:20:

(i) SEQUENCE CHARACTERISTICS:
        (A) LENGTH:324 base pairs
        (B) TYPE:nucleic acid
        (C) STRANDEDNESS:double
        (D) TOPOLOGY:linear (ii) MOLECULE TYPE:cDNA (ix) FEATURE:
        (A) NAME/KEY:mat peptide
        (B) LOCATION:1..324
        (C) IDENTIFICATION METHOD:E (xi) SEQUENCE DESCRIPTION:SEQ ID NO:20:
GAC ATC CAG ATG ACT CAG TCT CCA GCC TCC CTA TCT GCA TCT GTG GGA       48
Asp Ile Gln Met Thr Gln Ser Pro Ala Ser Leu Ser Ala Ser Val Gly
 1                5                  10                  15
GAA ACT GTC ACC ATC ACA TGT CGA GCA AGT GGG AAT ATT CAC AAT TAT       96
Glu Thr Val Thr Ile Thr Cys Arg Ala Ser Gly Asn Ile His Asn Tyr
                 20                  25                  30
TTA GCA TGG TAT CAG CAG AGA CAG GGA AAA TCT CCT CAG ATC CTG GTC      144
Leu Ala Trp Tyr Gln Gln Arg Gln Gly Lys Ser Pro Gln Ile Leu Val
         35                  40                  45
TAT AAT GCA AAA ACC TTA GCA GAT GGT GTG TCA TCA AGG TTC AGT GGC      192
Tyr Asn Ala Lys Thr Leu Ala Asp Gly Val Ser Ser Arg Phe Ser Gly
 50                  55                  60
AGT GGA TCA GGA ACA CAA TAC TCT CTC AAT ATC AAC AGC CTG CAG CCT      240
Ser Gly Ser Gly Thr Gln Tyr Ser Leu Asn Ile Asn Ser Leu Gln Pro
 65                  70                  75                  80
GAA GAT TTT GGG ACT TAT TTC TGT CAA CAT TTT TGG AGT ACT CCG TAC      288
Glu Asp Phe Gly Thr Tyr Phe Cys Gln His Phe Trp Ser Thr Pro Tyr
                 85                  90                  95
ACG TTC GGA GGG GGG ACC AAG CTG GAA ATA AAA CGG                      324
Thr Phe Gly Gly Gly Thr Lys Leu Glu Ile Lys Arg
                100                 105

(2) INFORMATION FOR SEQ ID NO:21:

(i) SEQUENCE CHARACTERISTICS:
        (A) LENGTH:414 base pairs
        (B) TYPE:nucleic acid
        (C) STRANDEDNESS:double
        (D) TOPOLOGY:linear (ii) MOLECULE TYPE:cDNA (ix) FEATURE:
        (A) NAME/KEY:sig peptide
        (B) LOCATION:1..57
        (C) IDENTIFICATION METHOD:E
        (A) NAME/KEY:mat peptide
        (B) LOCATION:58..414
        (C) IDENTIFICATION METHOD:E (xi) SEQUENCE DESCRIPTION:SEQ ID NO:21:
ATG AAA TGC AGC TGG GTT TTT CTC TTC CTG ATG GCA GTG GTT ACA GGG       48
Met Lys Cys Ser Trp Val Phe Leu Phe Leu Met Ala Val Val Thr Gly
            -15                 -10                  -5
```

```
GTC AAT TCA GAG GTT CAG CTG CAG CAG TCT GGG GCA GAG CTT GTG AAG        96
Val Asn Ser Glu Val Gln Leu Gln Gln Ser Gly Ala Glu Leu Val Lys
  1               5                  10
CCA GGG GCC TCA GTC AAA TTG TCC TGC ACA ACT TCT GGC TTC AAC ATC       144
Pro Gly Ala Ser Val Lys Leu Ser Cys Thr Thr Ser Gly Phe Asn Ile
         15                  20                  25
AAA GAC ATA TAT ATC TAC TGG GTG AAA CAG AGG CCT GAA CAG GGC CTG       192
Lys Asp Ile Tyr Ile Tyr Trp Val Lys Gln Arg Pro Glu Gln Gly Leu
 30              35                  40                  45
GAG TGG GTT GGA AGG ATT GAT CCT GCG AAT GGT GAT ACT AAA TAT GGC       240
Glu Trp Val Gly Arg Ile Asp Pro Ala Asn Gly Asp Thr Lys Tyr Gly
             50                  55                  60
CCG AAT TTC CAG GAC AAG GCC ACT ATA ACA GCA GAC ACA TCC TCC AAC       288
Pro Asn Phe Gln Asp Lys Ala Thr Ile Thr Ala Asp Thr Ser Ser Asn
                 65                  70                  75
ACA GCC TAC CTG CAG CTT CGT AGC CTG ACA TCT GAG GAC ACT GCC GTC       336
Thr Ala Tyr Leu Gln Leu Arg Ser Leu Thr Ser Glu Asp Thr Ala Val
             80                  85                  90
TAT TAC TGT GCT AGA CGG GGT AAC TAC GGG GCG GGG TTT GGT TAC TGG       384
Tyr Tyr Cys Ala Arg Arg Gly Asn Tyr Gly Ala Gly Phe Gly Tyr Trp
         95                 100                 105
GGC CAA GGG ACT CTG GTC ACT GTC TCT GCA                               414
Gly Gln Gly Thr Leu Val Thr Val Ser Ala
110                 115

(2) INFORMATION FOR SEQ ID NO:22:

(i) SEQUENCE CHARACTERISTICS:
        (A) LENGTH:384 base pairs
        (B) TYPE:nucleic acid
        (C) STRANDEDNESS:double
        (D) TOPOLOGY:linear (ii) MOLECULE TYPE:cDNA (ix) FEATURE:
        (A) NAME/KEY:sig peptide
        (B) LOCATION:1..60
        (C) IDENTIFICATION METHOD:E
        (A) NAME/KEY:mat peptide
        (B) LOCATION:61..384
        (C) IDENTIFICATION METHOD:E (xi) SEQUENCE DESCRIPTION:SEQ ID NO:22:
ATG AGT GTG CTC ACT CAG GTC CTG GCG TTG CTG CTG CTG TGG CTT ACA        48
Met Ser Val Leu Thr Gln Val Leu Ala Leu Leu Leu Leu Trp Leu Thr
-20                 -15                 -10                  -5
GGT GCC AGA TGT GAC ATC CAG ATG ACT CAG TCT CCA GCC TCC CTT TCT        96
Gly Ala Arg Cys Asp Ile Gln Met Thr Gln Ser Pro Ala Ser Leu Ser
              1                   5                  10
GCA TCT GTG GGA GAA ACT GTC ACC ATC ACA TGT CGA GCA AGT GGG AAT       144
Ala Ser Val Gly Glu Thr Val Thr Ile Thr Cys Arg Ala Ser Gly Asn
         15                  20                  25
ATT CAC AAT TAT TTA GCA TGG TAT CAG CAG AGA CAG GGA AAA TCT CCT       192
Ile His Asn Tyr Leu Ala Trp Tyr Gln Gln Arg Gln Gly Lys Ser Pro
     30                  35                  40
CAG ATC CTG GTC TAT AAT GCA AAA ACC TTA GCA GAT GGT GTG TCA TCA       240
Gln Ile Leu Val Tyr Asn Ala Lys Thr Leu Ala Asp Gly Val Ser Ser
 45              50                  55                  60
AGG TTG AGT GGC AGT GGA TCA GGA ACA CAA TAC TCT CTC AAT ATC AAC       288
Arg Phe Ser Gly Ser Gly Ser Gly Thr Gln Tyr Ser Leu Asn Ile Asn
             65                  70                  75
AGC CTG CAG CCT GAA GAT TTT GGG ACT TAT TTC TGT CAA CAT TTT TGG       336
Ser Leu Gln Pro Glu Asp Phe Gly Thr Tyr Phe Cys Gln His Phe Trp
                 80                  85                  90
AGT ACT CCG TAC ACG TTC GGA GGG GGG ACC AAG CTG GAA ATA AAA CGG       384
Ser Thr Pro Tyr Thr Phe Gly Gly Gly Thr Lys Leu Glu Ile Lys Arg
             95                 100                 105

(2) INFORMATION FOR SEQ ID NO:23:

(i) SEQUENCE CHARACTERISTICS:
        (A) LENGTH:248
        (B) TYPE:amino acid
        (D) TOPOLOGY:linear (ii) MOLECULE TYPE:peptide (xi) SEQUENCE DESCRIPTION:SEQ ID NO:23:
```

```
Glu Val Gln Leu Gln Gln Ser Gly Ala Glu Leu Val Lys Pro Gly Ala
 1               5                  10                  15
Ser Val Lys Leu Ser Cys Thr Thr Ser Gly Phe Asn Ile Lys Asp Ile
            20                  25                  30
Tyr Ile Tyr Trp Val Lys Gln Arg Pro Glu Gln Gly Leu Glu Trp Val
             35                  40                  45
Gly Arg Ile Asp Pro Ala Asn Gly Asp Thr Lys Tyr Gly Pro Asn Phe
         50                  55                  60
Gln Asp Lys Ala Thr Ile Thr Ala Asp Thr Ser Ser Asn Thr Ala Tyr
65                   70                  75                  80
Leu Gln Leu Arg Ser Leu Thr Ser Glu Asp Thr Ala Val Tyr Tyr Cys
                 85                  90                  95
Ala Arg Arg Gly Asn Tyr Gly Ala Gly Phe Gly Tyr Trp Gly Gln Gly
                100                 105                 110
Thr Leu Val Thr Val Ser Ala Gly Gly Gly Ser Gly Gly Gly Gly
            115                 120                 125
Ser Gly Gly Gly Gly Ser Asp Ile Gln Met Thr Gln Ser Pro Ala Ser
    130                 135                 140
Leu Ser Ala Ser Val Gly Glu Thr Val Thr Ile Thr Cys Arg Ala Ser
145                 150                 155                 160
Gly Asn Ile His Asn Tyr Leu Ala Trp Tyr Gln Arg Gln Gly Lys
                165                 170                 175
Ser Pro Gln Ile Leu Val Tyr Asn Ala Lys Thr Leu Ala Asp Gly Val
                180                 185                 190
Ser Ser Arg Phe Ser Gly Ser Gly Ser Gly Thr Gln Tyr Ser Leu Asn
            195                 200                 205
Ile Asn Ser Leu Gln Pro Glu Asp Phe Gly Thr Tyr Phe Cys Gln His
        210                 215                 220
Phe Trp Ser Thr Pro Tyr Thr Phe Gly Gly Gly Thr Lys Leu Glu Ile
225                 230                 235                 240
Lys Arg His His His His His His
                245
```

(2) INFORMATION FOR SEQ ID NO:24:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:24:

GGGAATTCAT GRAATGSASC TGGGTYWTYC TCTT                      34

(2) INFORMATION FOR SEQ ID NO:25:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:25:

CCCAAGCTTA GAGGGGGAAG ACATTTGGGA A                          31

(2) INFORMATION FOR SEQ ID NO:26:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:26:

ACTAGTCGAC ATGAGTGTGC TCACTCAGGT CCTGGSGTTG                40

(2) INFORMATION FOR SEQ ID NO:27:

```
    (i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:27:

GGATCCCGGG TGGATGGTGG GAAGATG                                       27

(2) INFORMATION FOR SEQ ID NO:28:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:28:

TCACTCGAGG CCACCATGAA ATGCAGCTGG GTT                                33

(2) INFORMATION FOR SEQ ID NO:29:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:29:

GAGGATCCTC CTCCTCCCGA TCCTCCTCCA CCTGCAGAGA CAGTGAC                 47

(2) INFORMATION FOR SEQ ID NO:30:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:30:

TCGGATCCGG AGGAGGAGGA TCGGACATCC AGATGACTCA G                       41

(2) INFORMATION FOR SEQ ID NO:31:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:31:

GAAGCGGCCG CATCATTAGT GATGGTGATG GTGATGCCGT TTTATTTCCA G            51
```

INTERLEUKIN-18-RECEPTOR PROTEINS

BACKGROUND OF THE INVENTION

1. Field of the Invention

This invention relates to a novel receptor protein recognizing a specific cytokine, more particularly, to a novel protein composing interleukin-18 receptor (hereinafter abbreviated as "IL-18R") or IL-18R protein, as well as to a monoclonal antibody specific to the IL-18R protein.

2. Description of the Prior Art

Interleukin-18 (hereinafter abbreviated as "IL-18) is a type of cytokine or substance which mediates signal transduction in immune system. As seen in Japanese Patent Kokai Nos.27,189/96 and 193,098/96 and Haruki Okamura et al., Nature, Vol.378; No.6,552, pp.88–91 (1995), IL-18 was provisionally designated as "interferon-gamma inducing factor" immediately after its discovery: This designation was changed later into "IL-18" in accordance with the proposal in Shimpei Ushio et al., The Journal of Immunology, Vol.156, pp.4,274–4,279 (1996). IL-18 in mature form consists of 157 amino acids and possesses properties of inducing in immunocompetent cells the production of interferon-gamma (hereinafter abbreviated as "IFN-γ") which is known as useful biologically-active protein, as well as of inducing and enhancing the generation and cytotoxicity of killer cells. Energetic studies are now in progress to develop and realize various uses of IL-18 in pharmaceuticals such as antiviral, antimicrobial, antitumor and anti-immunopathic agents which have been in great expectation because of these properties of IL-18.

As described above, in nature, cytokines including IL-18 are produced and secreted as substances responsible for signal transduction in immune system. Therefore, excessive amounts of cytokines may disturb the equilibria in immune system when they are produced or administered in the body of mammals. The surface of usual mammalian cells may bear certain sites or "receptors" which are responsible for recognition of cytokines: Secreted cytokines transduce no signal in cells till they are bound to the receptors. In normal immune system, there would be definite equilibria between respective cytokines and their receptors. Thus, in this field, with the purpose of developing and realizing IL-18 as pharmaceuticals, in addition to the clarification of physiological activities of IL-18, an expedited establishment of mass production and characterization of IL-18R protein have been in great expectation.

SUMMARY OF THE INVENTION

In view of the foregoing, the first object of this invention is to provide a receptor which recognizes IL-18.

The second object of this invention is to provide uses of the receptor as pharmaceuticals.

The third object of this invention is to provide a monoclonal antibody being reactive with the receptor.

The fourth object of this invention is to provide a hybridoma which is producible of the monoclonal antibody.

The fifth object of this invention is to provide a process to prepare the monoclonal antibody.

The sixth object of this invention is to provide a method to purify a receptor which recognize IL-18 using the monoclonal antibody.

The seventh object of this invention is to provide a method to detect a receptor which recognize IL-18 using the monoclonal antibody.

The eighth object of this invention is to provide an agent to detect a receptor which recognizes IL-18 using the monoclonal antibody.

The ninth object of this invention is to provide an agent to inhibit IL-18 using the monoclonal antibody.

The tenth object of this invention is to provide a method to inhibit IL-18 using the monoclonal antibody.

The eleventh object of this invention is to provide an agent to neutralize IL-18 using a receptor which recognizes IL-18.

The twelfth object of this invention is to provide a method to neutralize IL-18 using a receptor which recognizes IL-18.

We energetically and extensively screened various means which might attain these objects, eventually resulting in the finding that a substance which recognized IL-18 was present in L428 cell, a type of lymphoblastoid cell derived from a patient with Hodgkin's disease. We isolated and characterized this substance, revealing that its nature was proteinaceous, as well as that it well recognized and bound IL-18 even when in isolated form. It was also found that the IL-18R protein thus identified was efficacious in treatment and prevention of various diseases resulting from excessive immunoreaction, such as autoimmune diseases, because in mammals including human, the IL-18R protein recognized and neutralized IL-18 which activated immune system. Further, a hybridoma which is producible of a monoclonal antibody specific to the IL-18R protein was established by using as antigen the IL-18R protein, and the produced monoclonal antibody was confirmed to be useful for the purification and detection of the IL-18R protein, and confirmed to efficiently inhibit the physiological functions of IL-18. Thus we accomplished this invention.

More particularly, the first object of this invention is attained by IL-18R protein.

The second object of this invention is attained by an agent which contains as effective ingredient IL-18R protein.

The third object of this invention is attained by a monoclonal antibody specific to IL-18R protein.

The fourth object of this invention is attained by a hybridoma which is producible of the monoclonal antibody.

The fifth object of this invention is attained by a process to prepare monoclonal antibody, which comprises the steps of:

culturing in vitro or in vivo a hybridoma which is capable of producing a monoclonal antibody specific to IL-18R protein; and collecting the monoclonal antibody from the resultant culture or body fluid.

The sixth object of this invention is attained by a method to purify IL-18R protein, which comprises the steps of:

allowing a monoclonal antibody specific to the IL-18R protein to contact with a mixture of the IL-18R protein and contaminants to adsorb the IL-18R protein on the monoclonal antibody; and desorbing and collecting the IL-18R protein from the monoclonal antibody.

The seventh object of this invention is attained by a method to detect IL-18R protein, which comprises the steps of:

allowing a monoclonal antibody specific to the IL-18R protein to contact with a sample; and detecting the IL-18R protein through the occurrence of immunoreaction.

The eighth object of this invention is attained by an agent to detect IL-18R protein, which contains a monoclonal antibody specific to the IL-18R protein.

The ninth object of this invention is attained by an agent to inhibit IL-18, which contains as effective ingredient a monoclonal antibody specific to the IL-18R protein.

The tenth object of this invention is attained by a method to inhibit IL-18, which is characterized by allowing a monoclonal antibody specific to the IL-18R protein to act on the IL-18R protein.

The eleventh object of this invention is attained by an agent to neutralize IL-18, which contains as effective ingredient the IL-18R protein.

The twelfth object of this invention is attained by a method to neutralize IL-18, which is characterized by allowing the IL-18R protein to act on IL-18.

L428 cell, which is feasible in this invention, have been deposited in the Patent Microorganism Depository, National Institute of Bioscience and Human-Technology, Agency of Industrial Science and Technology, 1–3, Higashi 1 chome, Tsukuba-shi, Ibaraki-ken, 305, Japan, under the accession number of FERM BP-5777 on and after Dec. 24, 1996.

BRIEF EXPLANATION OF THE ACCOMPANYING DRAWINGS

DESCRIPTION OF THE SYMBOLS

Figure 1:
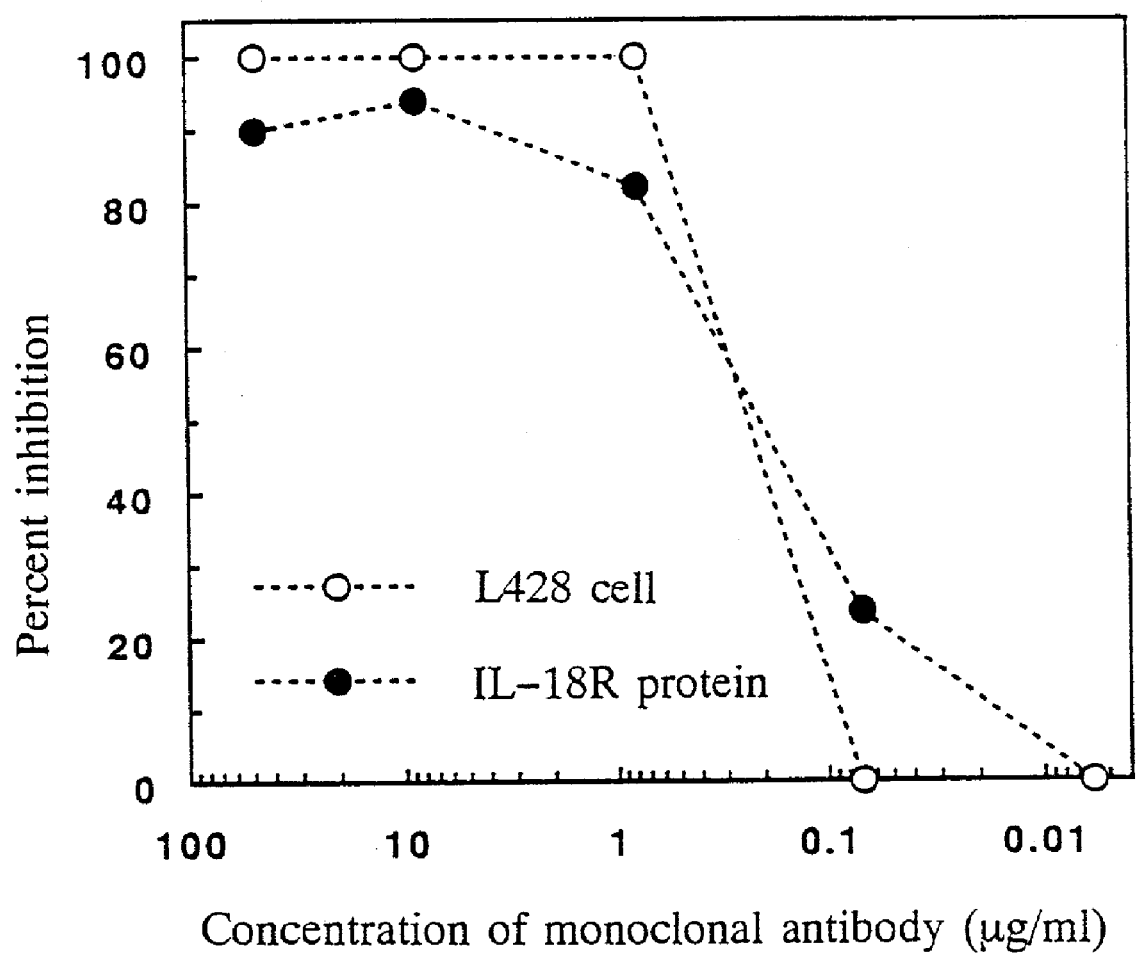
FIG. 1 shows that the monoclonal antibody MAb #117-10C binds to L428 cells and IL-18R while competing with IL-18.

The symbol "117-VL-VH cDNA" means the cDNA which encodes the variable regions of both the heavy and light chains in the monoclonal antibody MAb #117-10C.

The symbol "Pcmv" means the cytomegalo virus promotor.

DETAILED DESCRIPTION OF THE INVENTION

The IL-18R protein of this invention can be characterized by a property of recognizing IL-18. As to IL-18, those of human and mouse origins commonly consisting of 157 amino acids have been documented: Human IL-18 bears the amino acid sequence of SEQ ID NO:1 (where the amino acid with symbol "Xaa" represents either isoleucine or threonine), while mouse counterpart, the amino acid sequence of SEQ ID NO:2 (where the amino acid with symbol "Xaa" represents either methionine or threonine). The IL-18R protein has sites for recognizing and binding to IL-18. Binding of IL-18 to the sites expressed on immunocompetent cells can induce the production of IFN-γ in the cells. The IL-18R protein usually loses the property after being heated at 100° C. for 5 minutes. The IL-18R protein in an IL-18-bound form usually appears to have a molecular weight of about 50,000–200,000 daltons on sodium dodecyl sulfate-polyacrylamide gel electrophoresis (hereinafter abbreviated as "SDS-PAGE") in the presence of a reducing agent. The IL-18R protein may bear as partial amino acid sequence one or more amino acid sequences of SEQ ID NOs:3 to 10.

The IL-18R protein of this invention is obtainable from cells of mammals including human, based on the above property as a criterion. Examples of such cells are epithelial cells, endothelial cells, interstitial cells, chondrocytes, monocytes, granulocytes, lymphocytes, neurocytes, and established cell lines from these cells, preferably, those being expressing the IL-18R protein. Examples of particularly preferred cells are cell lines which are obtained by establishing hemopoietic cells including lymphocytes, in particular, JM cells, HDLM-2 cells, MOLT-16 cells and PEER cells described in Jun Minowada, *Cancer Review*, Vol.10, pp.1–18 (1988), and lymphoblastoid cells such as L428 cells (FERM BP-5777), KG-1 cells (ATCC CCL-246), and U-937 cells (ATCC CRL-1593.2), because they can easily proliferate and yield the IL-18R protein in desired amounts. To collect the IL-18R protein from the cells, the cells can be disrupted by a step such as ultrasonication after being cultured, and then, from the cell-disruptants, fractions with a protein which recognizes IL-18 can be collected. In case of culturing the cells, the yields of the IL-18R protein can be significantly increased by adding substances which induce the expression of the IL-18R protein in cells as mentioned above to the culture media, in particularly, by adding IL-12 or IL-18 at a dose of about 0.01 pg to 1 μg, preferably, about 1 pg to 100 ng per $1 \times 10^6$ cells. The responses to such substances are particularly remarkable in the hemopoietic cells. For example, in response to IL-12, some of the hemopoietic cells can yield the IL-18R protein twofold or higher. In collecting the IL-18R protein, a culture product is subjected to conventional methods common in purification of biologically-active proteins, for example, salting-out, dialysis, filtration, concentration, fractional precipitation, ion-exchange chromatography, gel filtration chromatography, adsorption chromatography, isoelectric focusing chromatography, hydrophobic chromatography, reversed phase chromatography, affinity chromatography, gel electrophoresis and isoelectric focusing gel electrophoresis which are used in combination, if necessary. Immnunoaffinity chromatographies using IL-18 itself or the monoclonal antibody of this invention, which are specific to the IL-18R protein, do yield a high-purity preparation of the IL-18R protein with minimized costs and labors.

The IL-18R protein of this invention exhibits a remarkable efficacy in treatment and prevention of various diseases resulting from excessive immunoreaction because in mammals including human, the IL-18R protein recognizes and binds IL-18 which may activate immune system. Immune system, which is in nature to defend living bodies from harmful foreign substances, may cause unfavorable results in living bodies because of its nature. When mammals receive a graft of organ, for example, skin, kidney, liver, heart and bone marrow, the rejection reaction and immunoreaction against alloantigen may activate T-cells, resulting in the occurrence of inflammation and proliferation of lymphocytes. Similar phenomena are observed in case that host receives the invasion by heteroantigens, for example, allergens which are not recognized as self. In autoimmune diseases, allergic reactions are induced by substances which must be recognized as self. The IL-18R protein of this invention exhibits a remarkable efficacy in treatment and prevention of various diseases resulting from such an immunoreaction because the IL-18R protein suppresses or regulates the immunoreaction when administered in mammals including human. Thus, the wording "susceptive diseases"

as referred to in this invention shall mean all the diseases resulting from augmented immunoreaction which can be treated and/or prevented by the direct or indirect action of the IL-18R protein: Particular susceptive diseases are, for example, rejection reactions associated with a graft of organ as described above, autoimmune and allergic diseases including pernicious anemia, atrophic gastritis, insulin-resistant diabetes, Wegener granulomatosis, discoid lupus erythematosus, ulcerative colitis, cold agglutinin-relating diseases, Goodpasture's syndrome, primary biliary cirrhosis, sympathetic ophtalmitis, hyperthyroidism, juvenile onset type diabetes, Sjögren syndrome, autoimmune hepatitis, autoimmune hemolytic anemia, myasthenia gravis, systemic scleroderma, systemic lupus erythematosus, polyleptic cold hemoglobinuria, polymyositis, periarteritis nodosa, multiple sclerosis, Addison's disease, purpura hemorrhagica, Basedow's disease, leukopenia, Behcet's disease, climacterium praecox, rheumatoid arthritis, rheumatopyra, chronic thyroiditis, Hodgkin's disease, HIV-infections, asthma, atopic dermatitis, allergic nasitis, pollinosis and apitoxin-allergy. In addition, the IL-18R protein of this invention is efficacious in treatment and prevention of septic shock which results from production or administration of excessive IFN-γ.

Thus, the agent for susceptive disease, which contains as effective ingredient the IL-18R protein of this invention, would find a variety of uses as anti-autoimmune-diseases, anti-allergies, anti-inflammatories, immunosuppressants, hematopoietics, leukopoietics, thrombopoietics, analgesics and antipyretics directed to treatment and/or prevention of susceptive diseases as illustrated in the above. The agent according to this invention is usually prepared into liquid, suspension, paste and solid forms which contain the IL-18R protein in an amount of 0.00001–100 w/w %, preferably, 0.0001–20 w/w %, dependently on the forms of agents as well as on the types and symptoms of susceptive disease.

The agent for susceptive diseases according to this invention includes those which are solely composed of the IL-18R protein, as well as including those in composition with, for example, one or more physiologically-acceptable carriers, excipients, diluents, adjuvants, stabilizers and, if necessary, other biologically-active substances: Examples of such stabilizer are proteins such as serum albumins and gelatin; saccharides such as glucose, sucrose, lactose, maltose, trehalose, sorbitol, maltitol, mannitol and lactitol; and buffers which are mainly composed of phosphate or succinate. Examples of the biologically-active substances usable in combination are FK506, glucocorticoid, cyclophosphamide, nitrogen mustard, triethylenethiophosphoramide, busulfan, pheniramine mustard, chlorambucil, azathioprine, 6-mercaptopurine, 6-thioguanine, 6-azaguanine, 8-azaguanine, 5-fluorouracil, cytarabine, methotrexate, aminopterin, mitomycin C, daunorubicin hydrochloride, actinomycin D, chromomycin $A_3$, bleomycin hydrochloride, doxorubicin hydrochloride, cyclosporin A, L-asparaginase, vincristine, vinblastine, hydroxyurea, procarbazine hydrochloride, adrenocortical hormone and auri colloid; receptor antagonists to cytokines other than IL-18, for example, antibodies respectively against interleukin-1 receptor protein, interleukin-2 receptor protein, interleukin-5 receptor protein, interleukin-6 receptor protein, interleukin-8 receptor protein and interleukin-12 receptor protein; and antagonists respectively against TNF-α receptor, TNF-β receptor, interleukin-1 receptor, interleukin-5 receptor and interleukin-8 receptor.

The agent for susceptive diseases according to this invention includes pharmaceuticals in minimal dose unit: The wording "pharmaceutical in minimal dose unit" represents those which are prepared into a physically united form suitable for prescription and also allowed to contain the IL-18R protein in an amount corresponding to its single dose or multiple (up to 4-fold) or divisor (up to ¼₀) thereof: Examples of such form are injection, liquid, powder, granule, tablet, capsule, sublingual, ophthalmic solution, nasal drop and suppository. The agent for susceptive diseases according to this invention can be administrated through both oral and parenteral routes to exhibit in each case a remarkable efficacy in treatment and prevention of susceptive diseases. More particularly, the IL-18R protein is administered through oral or parenteral route such as intradermal, subcutaneous, intramuscular or intravenous route at a dose of about 1 μg/time/adult to about 1 g/time/adult, preferably, about 10 μg/time/adult to about 100 mg/time/adult 1 to 4 times/day or 1 to 5 times/week over 1 day to 1 year.

This invention also relates to a monoclonal antibody specific to the IL-18R protein. The monoclonal antibody of this invention can be obtained by using as antigen the IL-18R protein or antigenic fragment thereof: more particularly, by preparing hybridoma cells of infinitely-proliferative cells of mammalian origin and antibody-producing cells from a mammal which has been immunized with such an antigen; selecting a clone of hybridoma which is capable of producing the monoclonal antibody of this invention; and culturing the clone in vitro or in vivo. The Il-18R protein is usually subjected to partial or complete purification prior to use as antigen, and the above mentioned process is feasible to obtain such IL-18R protein. To obtain an antigenic fragment, a partially- or completely-purified IL-18R protein is subjected to chemical or enzymatic degradation and, alternatively, peptide synthesis is conducted. Whole cells can be used as antigen, provided that they are in expression of the IL-18R protein.

Immunization of animal is conducted in conventional manner: For example, an antigen as described above is injected alone or together with an appropriate adjuvant in a mammal through intravenous, intradermal, subcutaneous or intraperitoneal route, and fed for a prescribed time period. There is no limitation in the type of mammals, therefore any mammals can be used regardless of their type, size and gender, as far as one can obtain desired antigen-producing cells therefrom. Rodents such as rat, mouse and hamster are generally used, and among these the most desirable mammal is chosen while considering their compatibility with the infinitely-proliferative cell to be used. The dose of antigen is generally set to about 5 to 500 μg/animal in total, which is divided into 2 to 20 portions and inoculated with time intervals of about 1 to 2 weeks, dependently on the type and size of mammal to be used. Three to five days after the final inoculation, the spleens are extracted and disaggregated to obtain spleen cells as antibody-producing cell.

The antibody-producing cell obtained in this way is then fused with an infinitely-proliferative cell of mammalian origin to obtain a cell fusion product containing an objective hybridoma. Examples of infinitely-proliferative cells usually used in this invention are cell lines of mouse myeloma origin such as P3/NSI/1-Ag4-1 cell (ATCC TIB-18), P3X63Ag8 cell (ATCC TIB-9), SP2/O-Ag14 cell (ATCC CRL-1581) and mutant strains thereof. Cell fusion can be conducted by conventional method using an electric pulse or a cell-fusion accelerator such as polyethylene glycol and Sendai virus: For example, antibody-producing cells and infinitely-proliferative cells of mammalian origin are suspended to give a ratio of about 1:1 to 1:10 in a cell fusion medium with such an accelerator and incubated at about 30 to 40° C. for about 1 to 5 minutes. Although conventional media such as minimum essential medium (MEM), RPMI-1640 medium and Iscove's modified Dulbecco's medium are feasible as cell fusion medium, it is desirable to remove the serum in media, such as bovine serum, prior to its use.

To select the objective hybridoma, the cell fusion product obtained as described above is transferred to an appropriate selection medium, such as HAT medium, and cultured at about 30 to 40° C. for 3 days to 3 weeks till the cells other than hybridoma died. The hybridoma cells are then cultured in usual manner and the antibodies secreted in the medium are tested for binding ability with the IL-18R protein. Such test can be conducted by conventional method directed to detection of antibodies in general, for example, enzyme immunoassay, radioimmunoassays and bioassay, which are detailed in *Tan-Clone-Kotai-Jikken-Manual* (Experimental Manual for Monoclonal Antibody), edited by Sakuji TOYAMA and Tamie ANDO, published by Kodansha Scientific, Ltd., Tokyo, Japan (1991), pp.105–152. The hybridoma which is capable of producing a monoclonal antibody specific to IL-18R protein is immediately cloned by the limiting dilution method, thus obtaining a monoclonalized hybridoma according to this invention.

The monoclonal antibody of this invention can be obtained by culturing such a hybridoma in vitro or in vivo. Culture of hybridoma is conducted by conventional methods which are common in cultivation of mammalian cells: More particularly, the monoclonal antibody can be collected from culture products in case of culturing in vitro on nutrient media, while in case of transplanting in non-human warm-blooded animals or culturing in vivo, the monoclonal antibody can be collected from the ascites and/or blood of the animals. The below mentioned hybridoma #117-10C has the merits that it is very high in productivity for the monoclonal antibody of this invention, as well as that it is easily culturable both in vitro and in vivo. To collect the monoclonal antibody from culture products, ascites and blood, conventional methods which are common in purification of antibodies general are used: Particular methods are, for example, salting-out, dialysis, filtration, concentration, fractional precipitation, ion-exchange chromatography, gel filtration chromatography, adsorption chromatography, isoelectric focusing chromatography, hydrophobic chromatography, reversed phase chromatography, affinity chromatography, gel electrophoresis and isoelectric focusing gel electrophoresis which are used in combination, if necessary. The purified monoclonal antibody is then concentrated and dehydrated into liquid or solid to meet to its final use.

Interleukin-6 (hereinafter abbreviated as "IL-6"), type of cytokine, is very useful in the preparation of the monoclonal antibody according to this invention. More particularly, in case of immunizing mammals with the antigen, IL-6 remarkably augments the antibody titer the mammals when IL-6 is administered by injection simultaneously with the inoculation of the antigen or before or after the inoculation. Further, the presence of IL-6 in cell fusion media to hybridize antibody-producing cells and infinitely-proliferative cells surprisingly increases the antibody-positive ratio in cell fusion and this extremely facilitates the cloning of hybridoma cells. While, the presence of IL-6 in culture media to proliferate a monoclonalized hybridoma accelerates the proliferation of the hybridoma and this remarkably augments the yield for the monoclonal antibody of this invention. Both natural and recombinant IL-6 preparations are equally feasible, provided that they originate from the same species of animal as those of the mammal and infinitely-proliferative mammalian cell to be used.

The monoclonal antibody of this invention also includes "humanized antibodies" which are usually prepared by the techniques in the protein engineering. To prepare a humanized antibody, for example, the mRNA is collected from a hybridoma of mammalian origin obtained as in the above, and exposed to the action of reverse transcriptase to obtain a cDNA which is then amplified by PCR method and cloned, thus determining the nucleotide sequences of heavy and light chains in the monoclonal antibody of this invention, desirably, those on variable regions in the heavy and light chains, followed by constructing a chimeric gene which encodes a polypeptide consisting of such variable regions and the constant regions found in human antibodies. Such a chimeric gene produces a monoclonal antibody with a binding specificity similar to that of the starting monoclonal antibody but with a remarkably decreased antigenicity to human when brought into expression in an appropriate host.

Further, a humanized antibody which bears the constant regions and the framework structures common in human antibodies and complementarily-determining regions (CDRs) essentially of a mammalian origin can be obtained by first determining the amino acid sequences of the CDRs, which constitute the antigen-binding sites on the heavy and light chains; then grafting these amino acid sequences and, if necessary, along with several amino acids located around the CDRs into a human antibody which bears a tertiary structure similar to that of the starting monoclonal antibody. The monoclonal antibody MAb #117-10C produced by the below mentioned hybridoma #117-10C of this invention contains in the variable regions of heavy and light chains the amino acid sequences of SEQ ID NOs:11 and 12 respectively, while in the hybridoma #117-10C, the amino acid sequences of SEQ ID NOs:11 and 12 are encoded by respective nucleotide sequences of SEQ ID NOs:19 and 20. In the monoclonal antibody #117-10C, the amino acid sequences of SEQ ID NOs:13–15 correspond to three types of CDRs on the heavy chain, i.e., CDR1, CDR2 and CDR3, while the amino acid sequences of SEQ ID NOs:16–18, three types of CDRs on the light chain, i.e., CDR1, CDR2 and CDR3. General methods for humanization of mammalian antibodies are known in the art as the relating techniques are described, for example, in *Methods in Molecular Biology*, Vol. 51, edited by S. Paul, published by Humana Press, Totowa, N.J. (1995).

The monoclonal antibody of this invention is particularly useful in immunoaffinity chromatographies to purify the IL-18R protein. The method to purify the IL-18R protein comprises the steps of allowing the monoclonal antibody of this invention to contact with a mixture of the IL-18R protein and contaminants to adsorb the IL-18R protein on the monoclonal antibody, and desorbing and collecting the IL-18R protein from the monoclonal antibody; these steps are usually carried out in aqueous conditions. The monoclonal antibody of this invention can be used after being immobilized on gels of water-insoluble carriers and being packed into columns. For example, the cell cultures or their partially purified mixtures are charged to such columns and run, resulting in that the IL-18R protein is substantially-selectively adsorbed by the monoclonal antibody on such carriers. The adsorbed IL-18R protein can be easily desorbed by altering the hydrogen-ion concentration around the monoclonal antibody. For example, the desorption for eluting the IL-18R protein is usually carried out under acidic conditions, preferably, pH 2-3 when using the monoclonal antibody belonging to immunoglobulin G (IgG), or alkaline conditions, preferably, pH 10-11 when using the monoclonal antibody belonging to immunoglobulin M (IgM). The present method do yield a high-purity preparation of the IL-18R protein with minimized costs and labors.

The monoclonal antibody of this invention additionally has wide uses in the agent for detecting the IL-18R protein. Using the monoclonal antibody in immunoassays with labels such as radioimmunoassays, enzyme immunoassays, and fluorescent immunoassays can make it more rapid and accurate to detect the IL-18R protein in samples qualitatively or quantitatively. In these immunoassays, the monoclonal antibody can be used after being labelled with radioactive substances, enzymes, and/or fluorescent substances. Because the monoclonal antibody usually specifically reacts with the IL-18R protein and exhibits immunoreaction, measuring the immunoreaction based on the labels can enable to accurately detect even a slight amount of the IL-18R protein in samples. The immunoassays using labels have a merit that they can analyze more numerous samples at a time and more accurately than bioassays. Thus the method to detecting the IL-18R protein of this invention is significantly useful for quality controls in processes for producing the IL-18R protein and their products, as well as for diagnoses of susceptive diseases that can be indicated by the levels of IL-18 and/or the IL-18R protein in body fluids. This invention, which may not basically relate to the techniques for labelling monoclonal antibodies or labelled assays, would not describe them in detail. Such techniques are detailed in a publication as P. Tisissen *Enzyme immunoassay*, translated by Eiji ISHIKAWA, published by Tokyo-Kagaku-Dojin, Tokyo, Japan(1989), pp.196–348.

The monoclonal antibody of this invention can act competitively with IL-18 for binding to the cells which are in expression of the IL-18R protein, leading to the inhibition of the physiological functions of IL-18 in mammals including humans. Thus the agent and method to inhibit IL-18 according to this invention are efficacious in treating various diseases to which IL-18 would be directly or indirectly related such as inflammations, allergoses, and autoimmune diseases, and in suppressing the rejections and excessive immunoreactions associated with grafting organs. The IL-18R protein bears the properties of recognizing and binding to IL-18, leading to the neutralization of its physiological functions. Thus the agent and method to neutralize IL-18 according to this invention where IL-18 is exposed to the IL-18R protein are efficacious in neutralizing IL-18 which is overproduced in or excessively administered to bodies. In addition, the IL-18R protein, bearing the properties of recognizing and binding to IL-18, must have uses in affinity chromatographies and labelled assays for purifying and detecting IL-18, similarly as the monoclonal antibody as described above. It can be additionally remarked that the IL-18R protein, the monoclonal antibody, and their fragments are useful as agents to screen agonists and antagonists to IL-18.

The following Examples explain this invention, and they can be diversified by the technical level in this field. In view of this, this invention should not be restricted to the Examples:

EXAMPLE 1

Preparation of IL-18R Protein

Newborn hamsters were intraperitoneally injected with an anti-lymphocyte antibody of rabbit origin to suppress their possible immunoreaction, subcutaneously injected at their dorsal areas with about $5 \times 10_5$ cell/animal of L428 cells (FERM BP-5777), a type of lymphoblastoid cell derived from a patient with Hodgkin's disease, and fed in usual manner for 3 weeks. The tumor masses, subcutaneously occurred, about 10 g each, were extracted, disaggregated and washed in usual manner in serum-free RPMI-1640 medium (pH 7.4), thus obtaining proliferated cells.

The proliferated cells were added with a mixture solution (volume ratio of 9:1) of 0.83 w/v % $NH_4Cl$ and 170 mM Tris-HCl buffer (pH 7.7) in an amount 10-fold larger than the wet weight of the cells, stirred and collected by centrifugation at 2,000 rpm for 10 minutes. The cells were then suspended in an appropriate amount of phosphate buffered saline (hereinafter abbreviated as "PBS"), stirred, collected by centrifugation at 2,000 rpm, resuspended to give a cell density of about $1 \times 10^8$ cells/ml in 10 mM Tris-HCl buffer (pH 7.2) with 1 mM $MgCl_2$ and disrupted with "POLYTRON", a cell disrupter commercialized by Kinematica AG, Littau/Lucerne, Switzerland. The resultant was added with 10 mM Tris-HCl buffer (pH 7.2) containing both 1 mM $MgCl_2$ and 1M sucrose to give a final sucrose concentration of 0.2M, and centrifuged at 1,000 rpm to collect the supernatant which was then centrifuged at 25,000 rpm for 60 minutes, followed by collecting the precipitate. The precipitate was added with adequate amounts of 12 mM 3-[(3-cholamidopropyl)dimethylammonio]-1-propanesulfonic acid (hereinafter abbreviated as "CHAPS"), 10 mM ethylenediaminetetraacetatic acid (hereinafter abbreviated as "EDTA") and 1 mM phenylmethylsulfonylfluoride, stirred at 4° C. for 16 hours, and centrifuged at 25,000 rpm for 60 minutes, followed by collecting the supernatant.

The supernatant was charged to a column of "WHEAT GERM LECTIN SEPHAROSE 6B", a gel product for affinity chromatography commercialized by Pharmacia LKB Biotechnology AB, Uppsala, Sweden, pre-equilibrated in PBS with 12 mM CHAPS, and the column was washed with PBS containing 12 mM CHAPS, and then charged with PBS containing both 0.5 M N-acetyl-D-glucosamine and 12 mM CHAPS while monitoring the protein content in the eluate with the absorbance of ultraviolet at a wave length of 280 nm. The fractions with an absorbance of 0.16–0.20 were collected and pooled, thus obtaining about 25 liters of aqueous solution with a protein content of about 1 mg/ml per $10^{12}$ starting cells.

A small portion of the solution was sampled, added with 4 ng human IL-18 which had been $^{125}$I-labelled in usual manner, incubated at 4° C. for 1 hour, added with appropriate amounts of "POLYETHYLENE GLYCOL 6000", a polyethylene glycol preparation with an averaged molecular weight of 6,000 daltons, commercialized by E. Merck, Postfach, Germany, and allowed to stand under ice-chilling conditions for 30 minutes to effect binding reaction. The reaction product was centrifuged at 6,000 rpm for 5 minutes and the resultant precipitate was collected to determine the level of radioactivity. In parallel, there was provided another sections as control in which 3 µg non-labelled human IL-18 was used along with $^{125}$I-labelled human IL-18 and treated similarly as above. Comparison with control revealed that the radioactivity of the sediment from the sample solution was significantly higher. This indicated that the aqueous solution obtained in the above did contain the IL-18R protein and the IL-18R protein recognized and bound IL-18 when exposed to IL-18.

EXAMPLE 2

Preparation of Hybridoma #117-10C

BALB/c mice were immunized with L428 cells, FERM BP-5777, in usual manner, by intraperitoneally injecting at a dose of $5 \times 10^7$ cells/body/shot 13 times during 6 months. Six and three days before extracted the spleens from the mice, 1 µg of the IL-18R protein, obtained by the method in Example 1, was peritoneally injected into the mice each. Three days after the final injection, spleens were taken out from the mice and dispersed to obtain splenocytes as antibody-producible cells.

The splenocytes and SP2/O-Ag14 cells, ATCC CRL-1581, derived from mouse myeloma, were co-suspended in serum-free RPMI-1640 medium (pH 7.2), prewarmed to 37° C., to give cell densities of $3 \times 10^4$ cells/ml and $1 \times 10^4$ cells/ml, respectively. The suspension was centrifuged to collect a precipitate. To the precipitate, 1 ml of serum-free RPMI-1640 medium containing 50 w/v % polyethylene glycol (pH 7.2) was dropped over 1 min, followed by incubating the resulting mixture at 37° C. for 1 min. Serum-free RPMI-1640 medium (pH 7.2) was further dropped to the mixture to give a final volume of 50 ml, and a precipitate was collected by centrifugation. The precipitate was suspended in HAT medium, and divided into 200 µl aliquots each for a well of 96-well microplates. The microplates were incubated at 37° C. for one week, resulting in 1,200 types of hybridoma formed. Supernatants from the hybridomas were analyzed by the two methods for studying the binding, described below in Example 3-2(a). By the analyses, a hybridoma which generated a supernatant that efficiently inhibited the binding of IL-18 to the IL-18R protein or L428 cells was selected. Conventional limiting dilution was repetitively applied to the selected hybridoma, and the hybridoma, #117-10C, producible of a monoclonal antibody according to this invention, was cloned.

EXAMPLE 3

Preparation and Characterization of Monoclonal Antibody MAb #117-10C

EXAMPLE 3-1

Preparation of Monoclonal Antibody MAb #117-10C

The hybridoma #117-10C obtained in Example 2 was suspended in RPMI-1640 medium supplemented with 10 v/v % fetal bovine serum (pH 7.2) to give a cell density of $1 \times 10^6$ cells/ml and cultured at 37° C. in a 5 v/v % $CO_2$ incubator while scaling up. After the cell density reached a desired level, $1 \times 10^7$ cells of the hybridoma #117-10C were intraperitoneally injected into BALB/c mice each, into which 0.5 ml of "PRISTANE", a reagent of 2,6,10,14-tetramethylpentadecane commercialized by Aldrich Chemical Co., Inc., Milwaukee, U.S.A., had been previously peritoneally injected, and the mice were fed in usual manner for one week.

The ascites were collected from the mice, and ammonium sulfate was added to the ascites to 60% saturation before allowing to stand at 4° C. for 5 hours. The resultants were centrifuged to collect a precipitate, which was then dissolved in 50 mM $KH_2PO_4$ (pH 6.8) and dialyzed against a fresh preparation of the same solution overnight. The dialyzed solution was charged to a column of hydroxyapatite. By running 100 mM $KH_2PO_4$ (pH 6.8) and 300 mM $KH_2PO_4$ (pH 6.8) through the column in this order, a monoclonal antibody MAb #117-10C according to this invention was eluted with 300 mM $KH_2PO_4$ in a yield of about 5 mg per one mouse. Analysis by conventional method proved that the monoclonal antibody MAb #117-10C belongs to a class of IgG.

EXAMPLE 3-2

Characterization of Monoclonal Antibody MAb #117-10C

EXAMPLE 3-2(a)

Binding Ability to IL-18R Protein

L428 cells (FERM BP-5777) were suspended in RPMI-1640 medium (pH7.4), supplemented with 0.1 v/v % bovine serum albumin and also containing 0.1 v/v % $NaN_3$, to give a cell density of $4 \times 10^7$ cells/ml, while a monoclonal antibody MAb #117-10C obtained by the method in Example 3-1 was dissolved in another preparation of RPMI-1640 medium supplemented with 0.1 w/v % bovine serum albumin to give different concentrations of 0.019 µg/ml, 0.209 µg/ml, 2.3 µg/ml, 25.3 µg/ml and 139.5 µg/ml.

Fifty microliter aliquots of the cell suspension prepared in the above were mixed with 50 µl of either solution with different monoclonal antibody concentrations, agitated at 4° C. for 2 hours, added with 50 µl of RPMI-1640 medium supplemented with 0.1 v/v % bovine serum albumin and also containing 4 ng $^{125}$I-labelled human IL-18 prepared in usual manner, and agitated at the same temperature for an additional 30 minutes. Subsequently, each cell suspension was added with 200 µl mixture solution (volume ratio 1:1) of dibutylphthalate and diocthylphtalate and centrifuged at 10,000 rpm and 20° C. for 5 minutes, followed by collecting the resultant precipitates containing the cells which were then determined for radioactivity using "MODEL ARC-300", a gamma-ray counter commercialized by Aloka Co., Ltd, Tokyo, Japan.

In parallel, there were provided additional two sections where the monoclonal antibody was neglected, while 4 ng $^{125}$I-labelled human IL-18 was treated similarly as in the sample with or without 4 µg of non-labelled human IL-18 (hereinafter referred to as "non-specific binding section" and "whole binding section" respectively). The levels of radioactivity found in "non-specific binding section" and "whole binding section" were put in Formula 1 together with that found in the sample testing section to calculate percent inhibition. The results were as shown in FIG. 1.

$$\text{Percent Inhibition} = \frac{\text{(Whole binding)} - \text{(Testing)}}{\text{(Whole binding)} - \text{(Non-specific binding)}} \times 100 \quad \text{Formula 1}$$

Fifty microliter aliquots of an aqueous solution of the IL-18R protein obtained by the method in Example 1 were added with 50 µl solution with different concentrations for monoclonal antibody MAb #117-10C prepared similarly as above, agitated at 4° C. for 2 hours, added with 4 ng $^{125}$I-labelled human IL-18, and agitated at 4° C. for an additional 30 minutes. Subsequently, each mixture was added with 50 µl of 4 mg/ml γ-globulin, allowed to stand under ice-chilling conditions for 30 minutes, added with 250

µl of PBS with 20 w/v % polyethylene glycol, allowed to stand under ice-chilling conditions for an additional 30 minutes, and centrifuged at 6,000 rpm at 4° C. for 5 minutes, followed by collecting the resultant precipitates which were then determined for radioactivity similarly as above.

At the same time, there were provided additional two sections where the monoclonal antibody was neglected, while 4 ng of $^{125}$I-labelled human IL-18 were treated similarly as in the sample with or without 4 µg of non-labelled human IL-18 (hereinafter referred to as "whole binding section" and "non-specific binding section"). The levels of radioactivity found in these two section were put in Formula 1 together in that found in the sample testing section to calculate percent inhibition. The results were as shown in FIG. 1.

As seen in FIG. 1, in both cases of using L428 cell and the IL-18R protein in solution, the binding of IL-18 to L428 cell and the IL-18R protein were inhibited much more as the concentration of monoclonal antibody MAb #117-10C elevated. This indicated that the monoclonal antibody MAb #117-10C was bound to the possible the IL-18R protein on the surface of L428 cell in a competing fashion with IL-18, as well as that the aqueous solution obtained by the method in Example 1 did contain a protein capable of recognizing IL-18 or the IL-18R protein and the monoclonal antibody MAb #117-10C specifically reacted with the IL-18R protein.

EXAMPLE 3-2(b)

Western Blotting

A portion of the IL-18R protein in aqueous solution obtained by the method in Example 1 was sampled, added with ⅔ volume of a mixture solution of 2.5 w/v % sodium dodecyl sulfate and 50 v/v % glycerol, incubated at 37° C. for 1 hour, and separated into respective proteinaceous components on conventional SDS-PAGE using 10–20% gradient gel but using no reducing agent. The proteinaceous components on the gel were transferred in usual manner to a nitrocellulose membrane which was then soaked for 1 hour in an appropriate amount of 50 mM Tris-HCl buffer (pH7.5) with 10 µg/ml of monoclonal antibody MAb #117-10C obtained by the method in Example 3-1, 10 v/v % "BLOCK ACE", an immobilizing agent commercialized by Dainippon Seiyaku Co., Ltd., Osaka, Japan, and 0.05 v/v % "TWEEN 20", a detergent commercialized by City Chemical Corp., New York, U.S.A., and washed in 50 mM Tris-HCl buffer (pH7.5) with 0.05 v/v % TWEEN 20 to remove the remaining antibody. The membrane was then soaked in Tris-HCl buffer (pH 7.5) with an appropriate amount of an anti-mouse immunoglobulin antibody of rabbit origin prelabelled with horse radish peroxidase, 10 v/v % "BLOCK ACE" and 0.05 v/v % "TWEEN 20" for 1 hour to effect reaction, washed in 50 mM Tris-HCl buffer (pH 7.5) with 0.05 v/v % "TWEEN 20" and developed using "ECL kit", a kit for development commercialized by Amersham Corp., Arlington Heights, U.S.A.

At the same time, there was provided another section without the monoclonal antibody MAb #117-10C as control and it was treated similarly as above. The molecular weight markers were bovine serum albumin (67,000 daltons), ovalbumin (45,000 daltons), carbonic anhydrase (30,000 daltons), trypsin inhibitor (20,100 daltons) and α-lactoalbumin (14,000 daltons). The results were as shown in FIG. 2.

Figure 2:
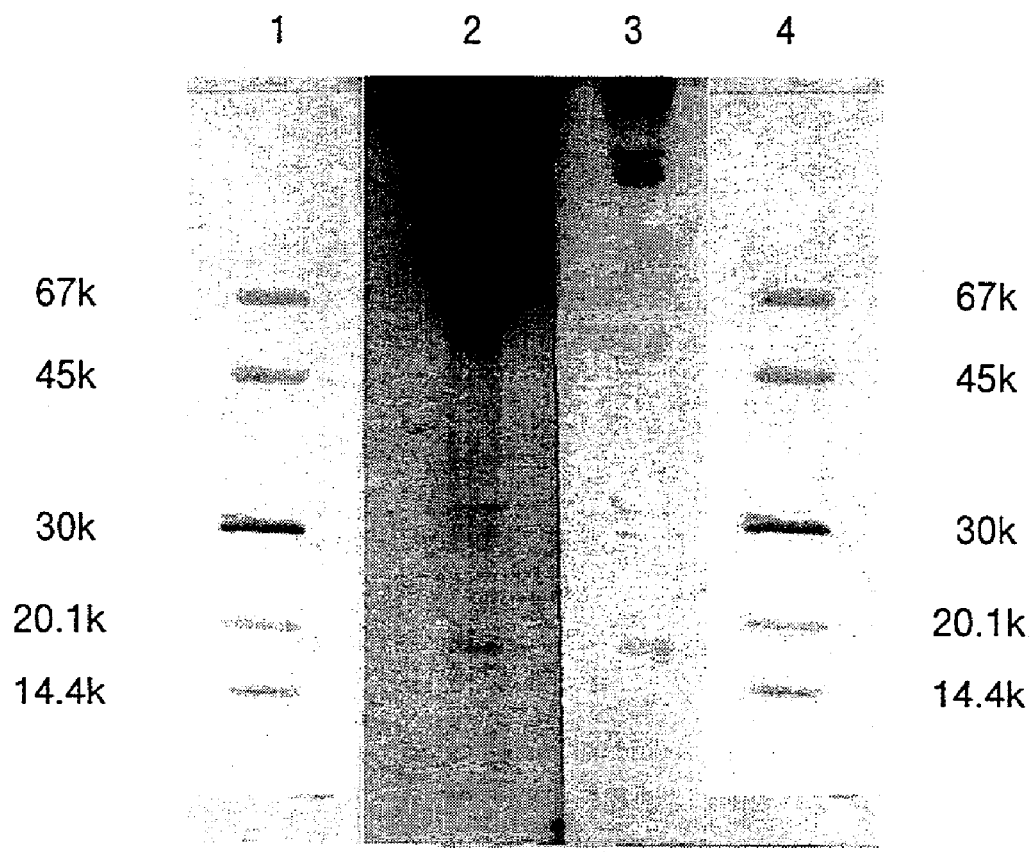
FIG. 2 is an image of intermediate tone given on display, which shows IL-18R on gel electrophoresis visualized by the Western blotting method using the monoclonal antibody MAb #117-10C.

In the gel electrophoresis in FIG. 2, Lane 2 (with monoclonal antibody) bore a distinct band of the IL-18R protein which was never found in Lane 3 (without monoclonal antibody).

EXAMPLE 3-2(c)

Inhibition of IL-18 Activity

KG-1 cells (ATCC CCL246), an established cell line derived from a patient with acute myelogenous leukemia, were suspended in RPMI-1640 medium (pH 7.2), supplemented with 10 v/v % fetal bovine serum and also containing 100 µg/ml kanamycin and 18.8 mM Na$_2$HPO$_4$, to give a cell density of 1×10$^7$ cells/ml, added with monoclonal antibody MAb #117-10C obtained by the method in Example 3-1 to give a concentration of 10 µg/ml and incubated at 37° C. for 30 minutes.

Figure 3:
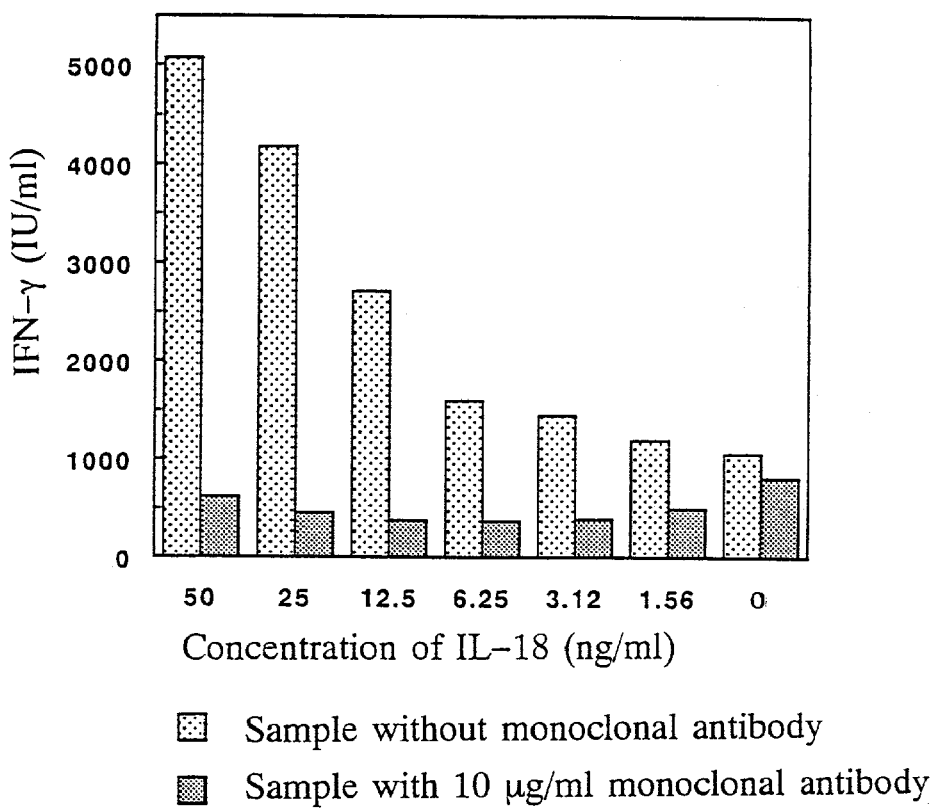
FIG. 3 shows the inhibitory action of the monoclonal antibody MAb #117-10C on the activity of IL-18.

The KG-1 cells in suspension were distributed on 96-well microplate to give respective amounts of 50 µl/well, added with 50 µl of human IL-18 which had been dissolved in a fresh preparation of the same medium to give respective concentrations of 0 ng/ml, 1.56 ng/ml, 3.12 ng/ml, 6.25 ng/ml, 12.5 ng/ml and 25 ng/ml, further added with 50 µl/well of 5 µg/ml lipopolysaccharide in a fresh preparation of the above medium, and incubated at 37° C. for 24 hours, after which each supernatant was collected and determined for IFN-γ content by conventional enzyme immunoassay. In parallel, there were provided additional sections without the monoclonal antibody MAb #117-10C for respective IL-18 concentrations as control and they were treated similarly as above. The results were as shown in FIG. 3. The IFN-γ contents in FIG. 3 were calibrated with reference to the standardized IFN-γ preparation Gg23-901-530 available from the International Institute of Health, USA, and expressed in the International Unit(IU).

The results in FIG. 3 indicated that the presence of monoclonal antibody MAb #117-10C inhibited the induction of IFN-γ by IL-18 in KG-1 cell as immunocompetent cell. This also indicated that monoclonal antibody MAb #117-10C blocked the IL-18R protein on the surface of KG-1 cell in a fashion competing with IL-18, thus preventing the signal transduction of IL-18 to KG-1 cell.

EXAMPLE 3-3

Amino-Acid Sequencing of Variable Regions and Identification of Complementarity-Determining Regions EXAMPLE 3-3(a)

Amino-Acid Sequence of Variable Region on Heavy Chain

In usual manner, the hybridoma #117-10C was suspended in RPMI-1640 medium supplemented with 10 v/v % fetal bovine serum and proliferated at 37° C. while scaling up cultivation. When the cell density reached a prescribed level, the proliferated cells were collected, suspended in 10 mM sodium citrate (pH7.0) containing both 6 M guanidine isothiocyanate and 0.5 w/v % sodium N-laurylsarcosinate, and then disrupted using a homogenizer.

Aliquots of 0.1M EDTA (pH 7.5) containing 5.7M CsCl$_2$ were injected in 35 ml-centrifugal tubes, and aliquots of the cell disruptant obtained in the above were placed in layer within each tube, after which the tubes were subjected to ultracentrifugation at 20° C. and 25,000 rpm for 20 minutes, followed by collecting and pooling the RNA fraction. The RNA fraction was distributed in 15-ml centrifugation tubes, added with equal volumes of chloroform/1-butanol (volume ratio 4:1), agitated for 5 minutes, and centrifuged at 4° C. and 10,000 rpm for 10 minutes to collect each aqueous layer which was then added with 2.5-fold volume of ethanol, and allowed to stand at −20° C. for 2 hours to effect precipitation of the total RNA. The total RNA was collected, washed with 75 v/v % aqueous ethanol, and dissolved in 0.5 ml of sterilized distilled water, thus obtaining an aqueous solution containing the total RNA from the hybridoma #117-10C.

The aqueous solution thus obtained was added with 0.5 ml of 10 mM Tris-HCl buffer (pH 7.5) containing both 1 mM EDTA and 0.1 w/v % sodium N-laurylsarcosinate to bring the total volume to 1 ml. The mixture solution was added with 1 ml of "OLIGOTEX™-dT30 <SUPER>", a latex with an oligonucleotide of $(dT)_{30}$ commercialized by Nippon Roche K. K., Tokyo, Japan, allowed to react at 65° C. for 5 minutes, and rapidly cooled in ice-chilling bath. The reaction mixture was added with 0.2 ml of 5 mM NaCl, allowed to stand at 37° C. for 10 minutes and centrifuged at 10,000 rpm for 10 minutes, after which the resultant precipitate was collected, suspended in 0.5 ml of sterilized distilled water, and allowed to stand at 65° C. for 5 minutes to desorb the RNA from the latex. The obtained aqueous solution was added with an appropriate amount of ethanol and the resultant precipitant was collected and lyophilized, thus obtaining a solid of mRNA.

Four microliters of 25 mM $MgCl_2$, 2 μl of 100 mM Tris-HCl buffer (pH 8.3) containing 500 mM KCl, 1 μl of 25 mM dNTP mix, 0.5 μl of 40 units/μl ribonuclease inhibitor and 1 μl of 200 units/μl reverse transcriptase were placed in 0.5 ml-reaction tube, added with 10 ng of the mRNA in solid obtained in the above along with an appropriate amount of random hexanucleotides, and added with sterile distilled water to bring the total volume to 20 μl. The resultant mixture in the tube was incubated first at 42° C. for 20 minutes, then at 99° C. for 5 minutes, thus obtaining a reaction mixture containing a first strand cDNA.

Twenty microliters of the reaction mixture was added with 1 μl of 2.5 units/μl "CLONED Pfu POLYMERASE", a DNA polymerase commercialized by Stratagene Cloning Systems, California, U.S.A., 5 μl of the reaction buffer and 1 μl of 10 mM dNTP mix, both commercialized by Stratagene Cloning Systems, further added with adequate amounts of oligonucleotides with the nucleotide sequences of 5'-GGGAATTCATGRAATGSASCTGGGTYW-TYCTCTT-3' (SEQ ID NO:24) and 5'-CCCAAGCTTA-GAGGGGGAAGACATTTGGGAA-3' (SEQ ID NO:25) as sense and antisense primers respectively, both chemically synthesized on the basis of the PCR primers described in Keizo Inoue et al., *Journal of Immunological Methods*, Vol.195, pp.27–32 (1996), added with sterilized distilled water to bring the total volume to 100 μl, and subjected to 35-time cycles of incubating at 94° C. for 1 minute, 50° C. for 2 minutes and 72° C. for 2 minutes in the given order to effect PCR reaction, thus obtaining a DNA fragment which contained the nucleotide sequence of SEQ ID NO:21.

EXAMPLE 3-3(b)

Amino-Acid Sequence of Variable Region on Light Chain

A reaction product containing the first strand cDNA, obtained by the method in Example 3-3(a), was treated similarly as in Example 3-3(a), except that sense and antisense primers were replaced with respective oligonucleotides with the nucleotide sequences of 5'-ACTAGTCGA-CATGAGTGTGCTCACTCAGGTCCTGGSGTTG-3' (SEQ ID NO:26) and 5'-GGATCCCGGGTGGATGGTGG-GAAGATG-3'(SEQ ID NO:27), both chemically synthesized on the basis of the PCR primers described in S. Tarran Jones et al., *BIO/TECHNOLOGY*, Vol.9, pp.88–89 (1991), thus obtaining another DNA fragment which contained the nucleotide sequence of SEQ ID NO:22.

EXAMPLE 3-3(c)

Identification of Complementarity-Determining Regions

Variable regions on light and heavy chains in antibodies resemble each other in structure, which generally comprise three CDRs and four framework structures linked via the CDRs. Further, in case of isologous antibodies, generally, the amino acid sequences of the framework structures are relatively well conserved, while a remarkable variation is found in the amino acid sequences of the CDR of particular antibody. Thus, we compared and collated the amino acid sequences determined in Examples 3-3(a) and 3-3(b) with those which have been documented for the variable regions in mouse antibodies, leading to the conclusion that in case of monoclonal antibody MAb #117-10C, the CDRs on the heavy chain bore the amino acid sequences of SEQ ID NO:13 (for CDR1), SEQ ID NO:14 (for CDR2) and SEQ ID NO:15 (for CDR3), while the CDRs on the light chain, the amino acid sequences of SEQ ID NO:16 (for CDR1), SEQ ID NO:17 (for CDR2) and SEQ ID NO:18 (for CDR3).

EXAMPLE 3-3(d)

Construction of Recombinant DNA Encoding Variable Regions

Ten nanograms of a DNA fragment encoding the variable region on the heavy chain, obtained by the method in Example 3-3(a), was added with 1 μl of 2.5 units/μl "CLONED Pfu POLYMERASE", a DNA polymerase commercialized by Stratagene Cloning Systems, California, U.S.A., 10 μl of the buffer commercialized by Stratagene Cloning Systems, California, U.S.A., and 1 μl of 25 mM dNTP mix, added with adequate amounts of oligonucleotides with the nucleotide sequences of 5'-TCACTCGAG-GCCACCATGAAATGCAGCTGGGTT-3' (SEQ ID NO:28) and 5'-GAGGATCCTCCTCCTCCCGATCCTC-CTCCACCTGCAGAGACAGTGAC-3' (SEQ ID NO:29) as sense and antisense primers respectively, and added with sterilized distilled water to bring the total volume to 100 μl. The mixture was subjected first to 3-time cycles of incubating at 94° C. for 1 minute, 42° C. for 2 minutes and 72° C. for 3 minutes in the given order, then to 35-time cycles of incubating at 94° C. for 1 minute, 60° C. for 2 minutes and 72° C. for 3 minutes in the given order to effect PCR reaction, thus obtaining a DNA fragment which consisted of the nucleotide sequence of SEQ ID NO:21, a digestion site for restriction enzyme XhoI and Kozak's sequence both linked to the 5'-terminal to the SEQ ID NO:21, and a digestion site for restriction enzyme BamHI and a sequence for a part of a linker both linked to the 3'-terminal to the SEQ ID NO:21.

Separately, 10 ng of a DNA fragment encoding the variable region on the light chain, obtained by the method in Example 3-3(b), was treated similarly above, except that the sense and antisense primers were replaced with oligonucleotides with respective nucleotide sequences of 5'-TCG-GATCCGGAGGAGGAGGATCGGACATCCA-GATGACTCAG-3' (SEQ ID NO:30) and 5'-GAAGCGGCCGCATCATTAGTGATGGT-GATGGTGATGCCGTTTTATTTCCAG-3'(SEQ ID NO:31), thus obtaining a DNA fragment which consisted of the nucleotide sequence of SEQ ID NO:20, a digestion site for restriction enzyme BamHI and a sequence for a part of a linker both linked to the 5'-terminal of the SEQ ID NO:20, and a digestion site for restriction enzyme NotI and a sequence for a tag of $(His)_6$ both linked to the 3'-terminal of the SEQ ID NO:20.

Figure 6:
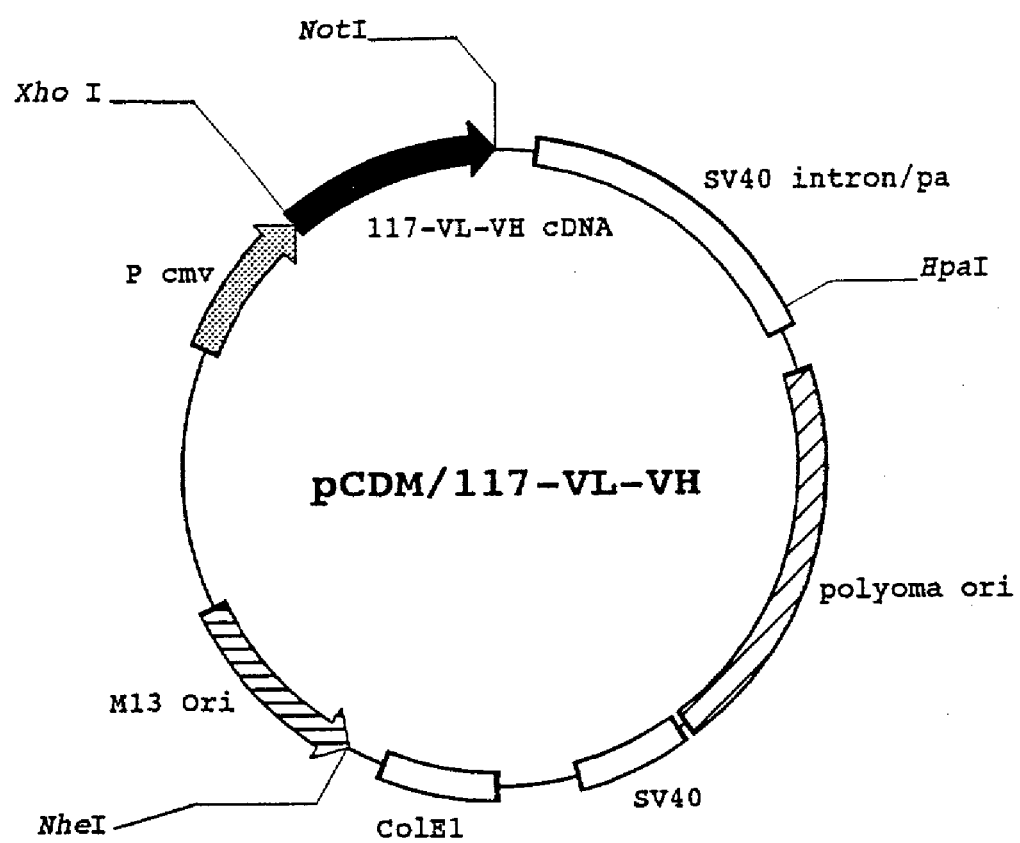
FIG. 6 shows the structure of the recombinant DNA "pCDM/117-VL-VH".

The two types of DNA fragments thus obtained were treated with restriction enzymes BamHI and either XhoI or NotI, added with 10 ng of "pCDM8", a plasmid vector commercialized by Invitrogen Corporation, San Diego, U.S.A., which had been digested with restriction enzymes XhoI and NotI, and allowed react using "LIGATION KIT VERSION 2", a ligation kit commercialized by Takara Shuzo Co., Ltd., Otsu, Shiga, Japan, at 16° C. for 2 hours, thus inserting the two types of DNA fragments in the plasmid vector. Thereafter, in usual manner, "MC1061/P3", an *Escherichia coli* strain commercialized by Invitrogen Corporation, San Diego, U.S.A., was transformed using the plasmid DNA, while the resultant transformant "CDM/117-VL-VH" was checked, revealed that in the cDNA "117-VL-VH cDNA" inserted in the transformant "CDM/117-VL-VH2, a cDNA "pCDM/117-VL-VH" encoding both variable regions on the heavy and light chains in the monoclonal antibody MAb #117-10C was linked to downstream of the cytomegalo virus promotor "Pcmv" as shown in FIG. 6.

EXAMPLE 3-3(e)

Preparation of Transformant and Expression of DNA

A transformant "CDM/117-VL-VH", obtained by the method in Example 3-3(d), was inoculated in LB medium (pH 7.5) containing both 20 μg/ml ampicillin and 10 μg/ml tetracycline and cultured at 37° C. for 18 hours, after which the cells was collected from the culture and treated in usual manner to obtain the plasmid DNA. Separately, COS-1 cells (ATCC CRL-1650), a fibroblastic cell line derived from the kidney of African green monkey, were proliferated in usual manner, while 20 μg of the plasmid DNA obtained in the above was introduced into $1 \times 10^7$ cells of the proliferated COS-1 cells by conventional electroporation method to obtain transformant cells. "ASF 104", a serum-free medium commercialized by Ajinomoto Co. Inc., Tokyo, Japan, was distributed in flat-bottomed culture bottles, inoculated with the transformed COS-1 cells to give a cell density of $1 \times 10^5$ cells/ml in each culture bottle, and cultured in usual manner at 37° C. in 5 v/v % $CO_2$ incubator for 4 days to express a polypeptide with the amino acid sequence of SEQ ID NO:23. The supernatant was collected from the culture and charged to a column of "Ni-NTA", a gel for affinity chromatography, commercialized by QIAGEN GmbH, Hilden, Germany, after which the column was applied first with PBS containing 20 mM imidazole to remove non-adsorbed components, then with PBS containing 250 mM imidazole while fractionating the eluate in a prescribed amount.

L428 cells (FERM BP-5777) were suspended in RPMI-1640 medium (pH 7.4), supplemented with 0.1 v/v % bovine serum albumin and also containing 0.1 w/v % $NaN_3$, to give a cell density of $1 \times 10^8$ cells/ml, and 50 μl aliquots of the cell suspension were added with 50 μl of either fraction obtained in the above, and agitated at 4° C. for 1 hour. Thereafter, each mixture was added with 4 ng of $^{125}$I-labelled human IL-18 in a fresh preparation of the same RPMI-1640 medium as described above to bring each final volume to 150 μl, agitated at 4° C. for an additional 30 minutes, placed in layer on 200 μl of dibuthylphthalate/dioctylphthalate (1:1 by volume), and centrifuged at 20° C. at 10,000 rpm for 5 minutes, after which the resultant precipitates were collected and examined for level of radioactivity using "MODEL ARC-300", a gamma-ray counter commercialized by Aloka Co., Ltd., Tokyo, Japan. As the result, the precipitates occurred from the fractions with the polypeptide were significantly lower in radioactivity than those from other fractions. This does confirm that the amino acid sequences of SEQ ID NOs:11 and 12 are those of the variable regions on the heavy and light chains in the monoclonal antibody MAb #117-10C respectively.

EXAMPLE 4

Purification and Partial Amino Acid Sequences of IL-18R Protein

EXAMPLE 4-1

Purification of IL-18R Protein

Seventy-eight milligrams of a monoclonal antibody MAb #117-10C, obtained by the method in Example 3-1, was dissolved in an appropriate amount of distilled water and the solution was dialyzed against borate buffer (pH 8.5) with 0.5M NaCl at 4° C. for 16 hours. Thereafter, in usual manner, an appropriate amount of "CNBr-ACTIVATED SEPHAROSE 4B", a CNBr-activated gel, commercialized by Pharmacia LKB Biotechnology AB, Uppsala, Sweden, was added to the dialyzed solution and allowed to react at 4° C. for 18 hours under gentle stirring conditions to immobilize the monoclonal antibody MAb #117-10C on the gel.

The gel was packed into column in a plastic cylinder, equilibrated with 2 mM CHAPS, charged with an aqueous solution of the IL-18R protein obtained by the method in Example 1, and applied with PBS with 12 mM CHAPS to remove non-adsorbed components. The column was then applied with 35 mM ethylamine containing 2 mM CHAPS (pH 10.8) while collecting the eluate in every 8 ml fractions which were then checked for presence of the IL-18R protein by the method in Example 1 using $^{125}$I-labelled human IL-18. The chromatogram obtained in this operation was as shown in FIG. 4.

Figure 4:
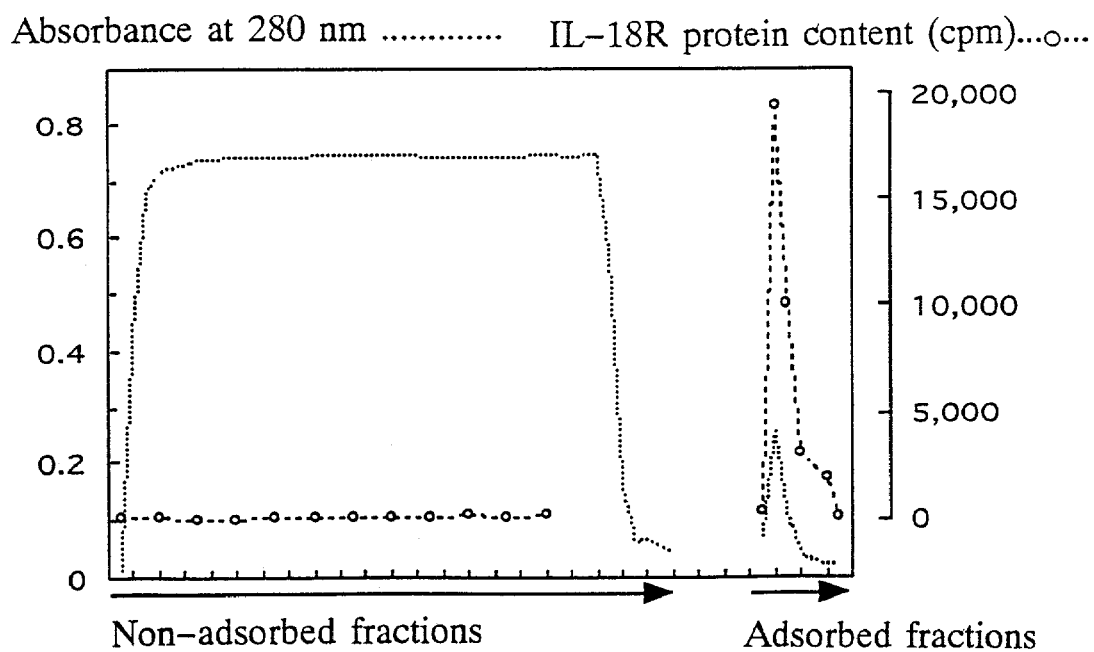
FIG. 4 is the chromatogram obtained by applying to IL-18R an immunoaffinity chromatography using the monoclonal antibody MAb #117-10C.

As seen in FIG. 4, the IL-18R protein was eluted in a single sharp peak when immunoaffinity chromatography using monoclonal antibody MAb #117-10C was applied to a mixture of the IL-18R protein and contaminants such as the aqueous solution of the IL-18R protein in Example 1. The fractions corresponding to this single peak were collected, pooled and lyophilized, thus obtaining a purified IL-18R protein in solid form.

Thereafter, a portion of the purified IL-18R protein was sampled, incubated in PBS at 100° C. for 5 minutes, and determined for residual activity by the method in Example 3-2(a), resulting in no binding to IL-18 which proved that the IL-18R protein was inactivated by heating. This would support that the nature of this receptor is proteinaceous.

Further, a portion of the purified IL-18R protein obtained in the above was dissolved in an appropriate amount of PBS, dialyzed against PBS at ambient temperature overnight, added with an appropriate amount of $^{125}$I-labelled human IL-18 prepared by the method in Example 1 and 1 mM "BS$^3$", a polymerizing agent commercialized by Pierce, Rockford, U.S.A., and allowed to stand at 0° C. for 2 hours to form a conjugate of the IL-18R protein and $^{125}$I-labelled human IL-18. The reaction mixture was added with Tris-HCl buffer (pH7.5), allowed to stand at 0° C. for an additional 1 hour to suspend the conjugation reaction, separated into respective proteinaceous components on SDS-PAGE using a set of molecular weight markers and dithiothreitol as reducing agent, and subjected to autoradiogram analysis.

The apparent molecular weight for this conjugate of the IL-18R protein and $^{125}$I-labelled human IL-18 was about 50,000 to 200,000 daltons when estimated with reference to the mobility of molecular weight markers on the autoradiogram. Since the molecular weight of IL-18 is about 20,000 daltons, the molecular weight of the IL-18R protein can be estimated about 30,000–180,000 daltons on the assumption that the IL-18R protein binds one human IL-18 molecule.

EXAMPLE 4-2

Peptide Mapping of IL-18R Protein

A purified IL-18R protein obtained by the method in Example 4-1 was electrophoresed on SDS-PAGE using 7.5 w/v % gel with 2 w/v % dithiothreitol as reducing agent, and the gel was soaked for 5 minutes in a mixture solution of 40 v/v % aqueous methanol and 1 v/v % acetic acid with 0.1 w/v % Coomassie Brilliant Blue for development, and soaked for an additional 2 hours for destaining in the same solution but without Coomassie Brilliant Blue, after which the stained part in the gel, molecular weight of 80,000–110,000 daltons, was cut off, added with 50 v/v % aqueous acetonitrile containing 0.2M $(NH_4)_2CO_3$ and repeatedly agitated at ambient temperature. Thereafter, the gel slices were lyophilized, added with 0.2M $(NH_4)_2CO_3$ (pH 8.0), allowed to stand for 5 minutes to effect swelling, added with appropriate amounts of 1 mM hydrochloric acid with 0.1 μg/μl "SEQUENCING GRADE MODIFIED TRYPSIN", a reagent of trypsin commercialized by Promega Corp., Madison, U.S.A., and 0.2M $(NH_4)_2CO_3$ (pH 8.9), and allowed to react at 37° C. overnight. After suspending with 10 v/v % aqueous acetic acid solution, the reaction mixture was added with a mixture solution of 0.1 v/v % trifluoroacetic acid and 60 v/v % aqueous acetonitrile and agitated at ambient temperature, after which the resultant supernatant was collected, concentrated in vacuo and centrifugally filtered, thus obtaining a concentrate with peptide fragments.

Figure 5:
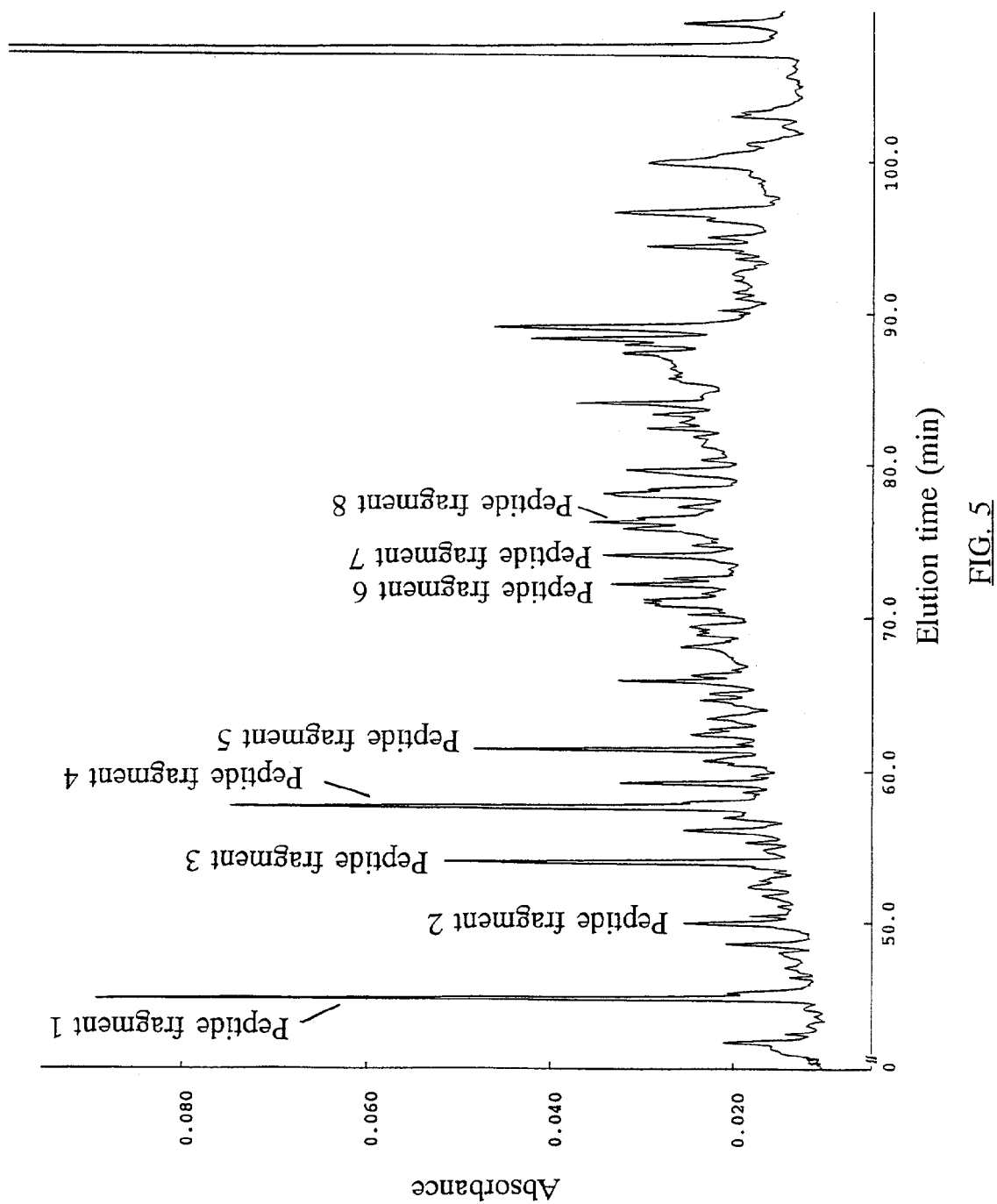
FIG. 5 is the peptide map of IL-18R.

The concentrate was charged to "μRPC C2/C18 SC2.1/10", a column for high-performance liquid chromatography commercialized by Pharmacia LKB Biotechnology AB, Uppsala, Sweden, pre-equilibrated with 0.065 v/v % trifluoroacetic acid, and then applied at a flow rate of 100 μl/min with 0.055 v/v % trifluoroacetic acid containing 80 v/v % aqueous acetonitrile liner gradient of acetonitrile increasing from 0 to 80 v/v % over 160 minutes immediately after application of eluent. While monitoring the absorbance at a wavelength of 240 nm, the eluate was fractionated to separately collect respective peptide fragments which eluted about 45, 50, 55, 58, 62, 72, 75 and 77 minutes after the application of the eluent. The peptide fragments (hereinafter referred to as "peptide fragment 1", "peptide fragment 2", "peptide fragment 3", "peptide fragment 4", "peptide fragment 5", "peptide fragment 6", "peptide fragment 7" and "peptide fragment 8" in the order of elution) were analyzed in usual manner for amino acid sequence using "MODEL 473A", a protein sequencer commercialized by Perkin-Elmer Corp., Norwalk, U.S.A, revealing that the peptide fragments 1 to 8 bore the amino acid sequences of SEQ ID NOs:3 to 10 respectively. The peptide map obtained by this operation was as shown in FIG. 5.

EXAMPLE 5

Liquid Agent

A purified IL-18R protein obtained by the method in Examples 4 was dissolved in physiological saline containing as stabilizer 1 w/v % "TREHAOSE", a powdered crystalline trehalose commercialized by Hayashibara Co., Ltd., Okayama, Japan, to give a concentration of 1 mg/ml, and the resultant mixture were sterilely filtered with membrane in usual manner to obtain a liquid agent.

The product, which is excellent in stability, is useful as injection, ophthalmic solution and collunarium in treatment and prevention of susceptive diseases including autoimmune diseases.

EXAMPLE 6

Dried Injection

One hundred milligrams of a purified IL-18R protein obtained by the method in Example 4 was dissolved in physiological saline containing 1 w/v % sucrose as stabilizer, the resultant solution was sterilely filtered with membrane, distributed in vials in every 1 ml aliquot, lyophilized and sealed in usual manner to obtain a pulverized agent.

The products, which is excellent in stability, is useful as dried injection in treatment and prevention of susceptive diseases including autoimmune diseases.

EXAMPLE 7

Ointment

"HI-BIS-WAKO 104", a carboxyvinylpolymer commercialized by Wako Pure Chemicals, Tokyo, Japan, and "TREHAOSE", a powdered crystalline trehalose commercialized by Hayashibara Co., Ltd., Okayama, Japan, were dissolved in sterilized distilled water to give respective concentrations of 1.4 w/w % and 2.0 w/w %, and an IL-18R protein obtained by the method in Example 1 was mixed with the resultant solution to homogeneity, and adjusted to pH7.2 to obtain paste agents containing about 1 mg/g of the IL-18R protein of this invention.

The products, which is excellent in both spreadablity and stability, is useful as ointment in treatment and prevention of susceptive diseases including autoimmune diseases.

EXAMPLE 8

Tablet

"FINETOSE", a pulverized anhydrous crystalline alpha-maltose commercilized by Hayashibara Co., Ltd., Okayama, Japan, was admixed with a purified IL-18R protein obtained by the methods in Examples 4 and "LUMIN" as cell activator, [bis-4-(1-ethylquinoline)][γ-4'-(1-ethylquinoline)] pentamethionine cyanine, to homogeneity, and the resultant mixture was tableted in usual manner to obtain tablets, about 200 mg each, containing about 1 mg/tablet of the IL-18R protein of this invention and also 1 mg/tablet of LUMIN each.

The product, which is excellent in swallowability and stability and also bears an cell activating property, is useful as tablet in treatment and prevention of susceptive diseases including autoimmune diseases.

Experiment

Acute Toxicity Test

In usual manner, a variety of agents, obtained by the methods in Examples 5 to 8, were percutaneously or orally administrated or intraperitoneally injected to 8 week-old mice. As the result, the $LD_{50}$ of each sample was proved about 1 mg or higher per body weight of mouse in terms of the amount of the IL-18R protein, regardless of administration route. This does support that the IL-18R protein of this invention is safe when incorporated in pharmaceuticals directed to use in mammals incuding human.

As explained above, this invention was made based on the discovery of a novel receptor protein which recognizes IL-18. The IL-18R protein of this invention exhibits a remarkable efficacy in relief of rejection reaction associated with grafts of organs and also in treatment and prevention of various disease resulting from excessive immunoreaction because the IL-18R protein bears properties of suppressing and regulating immunoreaction in mammals including human. Further, the IL-18R protein of this invention is useful in clarification of physiological activities of IL-18, establishment of hybridoma cells which are capable of producing monoclonal antibodies specific to the IL-18R protein.

The monoclonal antibody of this invention, specifically reacting with the IL-18R protein, is useful in particular for purification and detection of the IL-18R protein. Immunoaffinity chromatographies using the monoclonal antibody do yield a high-purity preparation of the IL-18R protein from a mixture of the IL-18R protein and contaminants with minimized labors and costs. The detection method using the monoclonal antibody accurately and rapidly detects even a slight amount of the IL-18R protein. The inhibiting method using the monoclonal antibody effectively inhibits the biological functions of IL-18, exhibiting a remarkable efficacy in treating the diseases resulting from the overproduction or excessive administration of IL-18. The monoclonal antibody, which bears outstanding usefulness, can be easily prepared in desired amounts by using the process according to this invention. In addition, the IL-18R protein, the monoclonal antibody and their fragments are useful in screening agonists and antagonists to IL-18R.

This invention, which exhibits these remarkable effects, would be very significant and contributive to the art.

While there has been described what is at present considered to be the preferred embodiments of the present invention, it will be understood the various modifications may be made therein, and it is intended to cover in the appended claims all such modifications as fall within the true spirits and scope of the invention.

We claim:

1. A process of preparing an IL-18 receptor protein, comprising:
   propagating a cell or cell line having all of the identifying characteristics of the cell line designated L-428 (FERM BP-5777),
   recovering the cells thus propagated, and
   isolating the IL-18 receptor protein from the cells;
   wherein the IL-18 receptor protein binds to IL-18, exhibits a molecular weight of 80–110 kDa on reducing SDS-PAGE, and comprises the amino acid sequences shown in SEQ ID NOs:3 to 10.

2. A method of inducing an antigenic response to an IL-18 receptor protein in a mammal, comprising administering a cell or cell line having all of the identifying characteristics of the cell line designated L-428 (FERM BP-5777) to the mammal in an amount effective to induce such response.

3. A method according to claim 2, further comprising the steps of recovering splenocytes from the mammal, fusing the splenocytes with a suitable fusion partner, culturing the hybridomas made thereby, and selecting a clone which expresses an antibody specific for an IL-18 receptor protein.

4. A method for suppressing immunoreaction or treating autoimmune disease induced by overproduction or administration of IL-18 in a mammal or human in need thereof, comprising assaying the level of IL-18 in said mammal or human and administering an IL-18 receptor protein as an effective ingredient in an amount effective to neutralize IL-18 in said mammal or human and suppress or treat the immunoreaction or the autoimmune disease induced by overproduction or administration of IL-18.

5. A method for treating an IL-18 receptor susceptive disease induced by overproduction or administration of IL-18 in a mammal or human in need thereof, comprising assaying the level of IL-18 in said mammal or human and administering an effective amount of an IL-18 receptor protein to neutralize IL-18 in said mammal or human, thereby treating the IL-18 receptor susceptive disease.

6. The method of claim 5, wherein said IL-18 receptor protein comprises the amino acid sequences shown in SEQ ID NOs: 3 to 10 as partial amino acid sequences, binds to IL-18, and exhibits a molecular weight of 80–110 kDa on reducing SDS-PAGE.

7. The method of claim 5, wherein the IL-18 receptor susceptive disease is selected from the group consisting of autoimmune diseases, allergic diseases, and rejection reactions associated with an organ graft.

* * * * *